(12) United States Patent
Kissel et al.

(10) Patent No.: US 8,518,444 B2
(45) Date of Patent: Aug. 27, 2013

(54) GRAFT COPOLYMERS AS DRUG DELIVERY SYSTEMS

(75) Inventors: Thomas Kissel, Staufen (DE); Xiaoying Wang, Guangzhou (CN)

(73) Assignee: Evonik Roehm GmbH, Darmstadt (DE)

( * ) Notice: Subject to any disclaimer, the term of this patent is extended or adjusted under 35 U.S.C. 154(b) by 609 days.

(21) Appl. No.: 12/677,602

(22) PCT Filed: Sep. 8, 2008

(86) PCT No.: PCT/EP2008/061854
§ 371 (c)(1),
(2), (4) Date: May 14, 2010

(87) PCT Pub. No.: WO2009/034053
PCT Pub. Date: Mar. 19, 2009

(65) Prior Publication Data
US 2010/0254939 A1  Oct. 7, 2010

(30) Foreign Application Priority Data
Sep. 11, 2007 (EP) .................................. 07116143

(51) Int. Cl.
*A61K 9/14* (2006.01)
(52) U.S. Cl.
USPC ........................................................ 424/486
(58) Field of Classification Search
USPC ........................................................ 424/486
See application file for complete search history.

(56) References Cited

U.S. PATENT DOCUMENTS

2001/0047074 A1   11/2001  Kissel et al.
2005/0113285 A1*  5/2005  Zhang et al. .................. 514/2

FOREIGN PATENT DOCUMENTS

DE   19839515 A1   3/2000
EP   1132416 A1    9/2001

OTHER PUBLICATIONS

Cai (Biodegradable polymer micro- and nanoparticles as protein delivery systems: influence of microparticle morphology and improvement of protein loading capacity of nanoparticles. Dissertation, Philipps-Universität Marburg Sep. 20, 2007).*
Breitenbach et al.; Biodegradable comb polyesters: Part 1 Synthesis, characterization and structural analysis of poly(lactide) and poly(lactide-co-glycolide) grafted onto water-soluble poly(vinyl alcohol) as backbone; Polymer; 1998; vol. 39; No. 14; pp. 3261-3271.
Breitenbach et al.; Biodegradable comb polyesters. Part II. Erosion and release properties of poly(vinyl alcohol)-g-poly(lactic-co-glycolic acid); Polymer; 2000; Vo.. 41; pp. 4781-4792.
Pistel et al.; Brush-like branched biodegradable polyesters, part III Protein release from microspheres of poly(vinyl alcohol)-graft-poly(D,L-lactic-co-glycolic acid); Journal of Controlled Release; 2001; vol. 73; pp. 7-20.
International Search Report, Form PCT/ISA/210, for corresponding PCT/EP2008/061854.

* cited by examiner

*Primary Examiner* — Benjamin Packard
(74) *Attorney, Agent, or Firm* — Oblon, Spivak, McClelland, Maier & Neustadt, L.L.P.

(57) ABSTRACT

The present invention relates to graft copolymers of polyvinyl sulfonic-co-vinyl alcohol)-g-poly(lactide-co-glycolide) (P(VS-VA)-g-PLGA) with negatively charged electrolyte properties, their method of preparation and their use. These negatively charged graft copolymers are suitable for effective loading and sustained-release of especially positively charged drugs, proteins and peptides, and drug-loaded particles from these grafted co-polymers are especially useful as parenteral or mucosal drug delivery systems for pharmaceutical applications.

49 Claims, 10 Drawing Sheets

A. Radical copolymerization of vinyl sulfonic acid sodium and vinyl acetate

B. Hydrolysis to obtain poly(vinyl sulfonic-co-vinyl alcohol)

C. Graft PLGA(LA:GA=50:50)

R = H (GA) or CH$_3$ (LA)

LA: R= CH₃, 1+1'+2+2'

GA: R= H, 3+3'

LA: R= CH$_3$, 1+1'+2+2'+4+4'

GA: R= H, 3+3'+5+5'

GRAFT COPOLYMERS AS DRUG DELIVERY SYSTEMS

FIELD OF THE INVENTION

The present invention relates to the field of drug delivery systems. It describes graft copolymers of poly(vinyl sulfonic-co-vinyl alcohol)-g-poly(lactide-co-glycolide) (abbreviated as P(VS-VA)-g-PLGA, with negatively charged electrolyte properties, their method of preparation and their use. These negatively charged graft copolymers are suitable for effective loading and sustained-release of especially positively charged drugs, proteins and peptides; drug-loaded particles from these grafted co-polymers are especially useful as parenteral or mucosal drug delivery systems for pharmaceutical applications.

BACKGROUND OF THE INVENTION

The protection of biologically and/or pharmaceutically active substances like drugs and especially proteins intended to be applied for medical uses against denaturation and enzymatic degradation is an important issue for all drug delivery systems. Also the controlled release of such active compounds, including small molecules, after application and the enhancement of transport across mucosal surfaces remain important issues.

Polymeric excipients as possible drug delivery systems are in principle known in the state of the art. Possible strategies based on polymeric carriers for mucosal and parenteral delivery of proteins include for example (a) modification of biologically active compounds with polymers, (b) encapsulation of the hydrophilic macromolecules into micro- or nanospheres or micro- or nanoparticles, and (c) adsorptive drug loading onto the surface of micro- or nanospheres or micro- or nanoparticles. Because of their medical use these systems are also required to be bio-degradable.

This challenge is especially important for oral, mucosal and parenteral systems designed for hydrophilic, especially macromolecular ingredients. Additionally, each requirement differs with regard to the specific envisaged application, which motivates a search for chemically diverse polymers.

Some polymers have already been developed to meet these requirements, but there still remains a formidable challenge since structure function relations of suitable polymers are still scarce. A certain approach aims at the identification of negatively charged polymers, especially polyesters as carriers for pharmacologically active substances because these are expected to be particularly suitable for effective loading and to exhibit sustained-release properties of positively charged drugs, proteins and peptides.

Biodegradable matrix polymers for active ingredient embedding have already been described in U.S. Pat. No. 3,773,919. Polymers from hydroxycarboxylic acids, especially lactic and/or glycolic acid were proposed. However, depot forms from polylactic acid (PLA) or polylactic-co-glycolic acid (PLGA), especially microparticles, generally exhibit a multiphase release trend and initially display a sharply increased release because of active ingredient present on the surface. This is followed by a phase of sharply reduced or nonexistent release, especially in peptide active ingredients, which is then followed by later active ingredient liberation supported by polymer mass degradation. Polymer residues are still present at the time of completion of active ingredient release.

EP 058481 A1 describes the use of a mixture of PLGA having different molecular weights. Drug release is supposed to be linearized by this and the degradation rate adjusted to the release period. Use of such polymer mixtures, however, imposes high requirements on the hydrolytic stability of the active ingredient and they are generally not well suited for the production of microparticles.

DE 3430852 A1 describes esters from polyols and poly- or copolylactic acid, which are also proposed as matrix polymers for depot forms. Example 26 entails in-vitro release of washed microparticles containing bromocriptin mesylate produced by spray drying. Despite washout of the active ingredient adhering to the microparticle surface, after 24 hours 62% of the active ingredient load had already been released.

EP 407617 A1 describes a biocompatible polyester with increased hydrolysis rate consisting of saccharides bonded to PLA or PLGA. The polyesters are proposed as matrix material for depot forms. However, they seem to be associated with the problem of nonuniform active ingredient release and especially the problem of the initial burst effect.

Additionally, polyesters consisting of a polysaccharide backbone are thermally not very stable during the grafting reaction, and are also less soluble in monomer melt as compared to polyesters with a polyvinyl backbone. In addition, the presence of the naturally occurring saccharide may imply the risk of possible immunogenic reactions in vivo. Furthermore, these polymers show bulk erosion.

DE 19839515 A1 discloses the colloidal association of an active agent like a peptide, a DNA construct or a vaccine with a polyol ester which together in the form of a colloid are to be used as a pharmaceutical preparation for controlled transmucosal administration. The disclosed polymers for such a use are branched polyol esters consisting of a central molecule to which short-chain, biodegradable hydroxycarboxylic acid ester groups are attached.

Polymers, based on a polyvinyl alcohol backbone are described in the publication "Biodegradable comb polyesters: Part 1; synthesis, characterization and structural analysis of poly(lactide) and poly(lactide-co-glycolide) grafted onto water-soluble poly(vinyl alcohol) as backbone" by Breitenbach et Kissel, *Polymer*, 39 (14): 3261-3271 (1998). Based on an analysis of their physicochemical properties they are described as having considerable potential as a parenteral drug delivery system for peptides and proteins.

Patent application EP 1132416 A1 discloses colloidal nanoparticular carriers comprising loaded or non-loaded water soluble comb polymers and their use in mucosal applications. They are characterized by a backbone formed from water-soluble polyol(s) grafted with hydrophobic side-chains, providing an amphiphilic character, and optionally ionic groups, where the backbone polymer has a weight average molecular weight (Mw) of 10,000-30,000 g/mol and the side-chains preferably have a combined Mw of 45,000-100,000 g/mol. Such colloidal nanoparticular carriers are described as being useful as drug delivery systems for especially large biomolecules like proteins and nucleic acids. Unfortunately, because of their ability to attach to mucous membranes (bio-adhesion) they are expected to induce a systemic immune response.

US patent application US 2001/0047074 A1 (granted as U.S. Pat. No. 6,616,944 B2) discloses self-assembling, polymer-based delivery systems for proteins. The delivery systems comprise an active agent and a polyol ester, having a linear polyol containing six or more hydroxyl groups as a central backbone and biodegradable hydroxy carboxylic ester groups attached to the central backbone; as an additional feature of these systems, the linear polyol contains charged groups, proton donating groups, and/or proton accepting groups, which are attached via a spacer group or an ether-, ester-, or urethane-linkage to the linear polyol. Such delivery systems are described to form stable complexes with proteins and therefore as being useful as drug carriers for therapeutic use or vaccines.

Unfortunately, co-polyesters of just lactic and glycolic acid (PLGA) turned out to be suboptimal for protein and DNA delivery due to inactivation by the acidic microenvironment and uncontrolled burst release due to poor compatibility between lipophilic polymers and hydrophilic drug candidates.

One proposed solution to address these problems associated with PLGA has been to introduce the hydrophilic composition with functional group to this polyester system, leading to first copolymers of PLGA and poly(ethylene glycol) (PEG), as described e.g. in: Youxin, L., Kissel T.: Synthesis and properties of biodegradable ABA triblock copolymers consisting of poly(L-lactic acid) or poly(L-lacticgo-glycolic acid) A-blocks attached to central poly(oxyethylene) B-blocks; *J. Control Release* 1993; vol. 27, pages 247-257.

Subsequently described approaches have been:
the development of star branched poly(lactide)s (PLAs) and PLGs with low molecular multifunctional alcohols, like glycerol, pentaerythritol, mannitol/sorbitol or star-shaped poly(ethylene glycol)s, as described e.g. in: S. H. Kim et al.: Preparation of star-shaped polylactide with pentaerythritol and stannous octoate; *Makromol. Chem.*, vol. 194 (1993), pages 3229-3236;

using comb-like, highly branched polyesters synthesized by grafting sulfonic modified dextran based, backbones with lactide and glycolide, which allow a faster biological degradation with negatively charged groups, as described e.g. in: Li et al.: Biodegradable brush-like graft polymers from poly(D,L-lactide) or poly(D,L-lactide-co-glycolide) and charge-modified, hydrophilic dextrans as backbone-Synthesis, characterization and in vitro degradation properties; *Polymer* 1997; vol. 38, pages 6197-6206;

the synthesis of biodegradable comb PLGA by grafting short PLGA chains onto different poly(vinyl alcohol) (PVA) based backbone polyols, poly(2-sulfobutyl vinyl alcohol) and poly(diethylaminoethyl-vinyl alcohol). In this system, the adjustment of the polymer-properties were carried out by introducing charged groups sulfobutyl moieties or amine structures into the PVA backbone, to create polymers with negative or positive charges, as described e.g. in: Breitenbach A, Kissel T.: Biodegradable comb polyester: Part 1. Synthesis, characterization and structural analysis of poly(lactide) and poly(lactide-co-glycolide) grafted onto water-soluble poly(vinyl alcohol) as backbone; *Polymer,* 1998; vol. 39: pages 3261-3271.

By another approach to effectively load positively charged drugs, proteins and peptides, functional groups were introduced to the drug delivery systems, such as hydroxycarboxylic groups, as disclosed e.g. in WO 95/23175 A1.

Also through the NaH activation method the sulfobutylated PVA were obtained and using them to graft PLGA, the negatively charged poly(2-sulfobutyl vinyl alcohol)-g-PLGA were prepared, leading to a better temperature stability during bulk polymerization with PLGA (Breitenbach A. et al.: Biodegradable comb polyesters containing polyelectrolyte backbones facilitate the preparation of nanoparticles with defined surface structure and bioadhesive properties; *Polym. Adv. Technol.;* 2002; vol. 13, pages 938-950).

Because of the NaH activation method the synthesis of the negatively charged poly(2-sulfobutyl vinyl alcohol)-g-PLGA is difficult to control with respect to the degree of substitution which can be reached through the introduction of the sulfobutyl groups to the PVA backbone.

Additionally, the sulfobutylation approach does provide only a small range of variations of the degree of substitution with negative charges.

As can be seen from these explanations there still exists a need for further polymers, which are better suitable as appropriate carriers for biologically or pharmacologically active substances and which allow effective loading and sustained-release of especially positively charged drugs, proteins and peptides from micro- or nanospheres or micro- or nanoparticles as polymeric drug delivery systems. It must be kept in mind that these pharmacologically active substances make up a quite diverse group of molecular entities, characterized by different physicochemical properties and different requirements with regards to the application.

It is therefore an aim of the present invention to provide a set of novel polymers which could be used as polymeric drug delivery systems (polymeric excipients) for at least one, preferably more classes of pharmaceutically active ingredients.

It is an additional task to provide polymers which are especially well suited as carriers for biologically and/or pharmacologically active molecules like proteins and peptides and drugs, especially those which are cationic and/or positively charged. The overall biophysical properties of such materials had to be specifically designed to allow modifications of the drug loading and degradation behaviour of the desired drug delivery system.

It is a further task to provide polymers which allow the preparation of micro- or nanoparticles and of self-aggregating colloidal systems with defined and finely adjustable surface properties. Preferably this preparation of micro- or nano-particulate systems should be possible even without the use of surfactants in the water phase during their preparation, thus qualifying the resulting polymers for the use in the respiratory tract.

As a solution to these problems the present invention provides graft copolymers of poly(vinyl sulfonic-co-vinyl alcohol)-g-poly(lactide-co-glycolide) (P(VS-VA)-g-PLGA) with negatively charged electrolyte properties.

Graft copolymers according to the invention provide novel polymeric excipients with hitherto unknown properties which make them well suited as drug delivery systems. These systems allow effective loading and sustained-release of drugs, proteins and peptides, especially for medical applications. They can also be applied to the preparation of drug-loaded particles, microparticles and nanoparticles and self-aggregating colloidal systems. Drug delivery systems based on this material are especially useful as parenteral or mucosal drug delivery systems for pharmaceutical applications.

The amphiphilic and negatively charged nature of the graft copolymers according to the invention allows a better drug loading by electrostatic interactions as a function of sulfonic substitution. They are suitable for generally all pharmacologically active substances and for effective loading and sustained-release of such active substances, especially of positively charged drugs, proteins and peptides.

The particular advantage of this polymer type is the broad range of the degree of substitution with negative charges which cannot be achieved by e.g. sulfobutylation.

Thus it is an advantage of graft copolymers according to the invention that they can reproducibly be synthesized with even minute variations of the chemical structure. For example, the degree of sulfonic substitution and the degree of PLGA substitution as well as composition of the PLGA side chains can be designed. This also allows the preparation of micro- and nanoparticles and self-aggregating colloidal systems with accurately defined properties such as inertness against drugs or biopolymers like proteins or nucleic acids, intrinsic viscosity, solubility, melting point, glass transition temperature, hydrophilicity/hydrophobicity (amphiphilic nature), rate of degradation and surface charge. Especially the substitution degree of negative charges can be varied over a wide range, which is wider e.g. than the respective variation degree of sulfobutyl-polyvinylalcohol—graft PLGA (SB-PVAL-g-PLGA).

For example a system according to the invention can be designed for the loading with positively charged drugs like Salbutamol, Ipratropiumbromid or Tiotropiumbromid or others (see below). The charge allows a slower release of the drug in vivo in comparison to a more neutral material.

Additionally, in most cases the preparation of micro- and nanoparticles and self-aggregating colloidal systems from these polymers is possible even without the use of surfactants in the water phase.

These polymers combine, within a modified three-dimensional architecture, increased hydrophilicity (due to the grafted side chains) and negatively charged groups (due to the vinyl sulfonic) in a single polymer, all of which can be precisely synthesized.

Due to the existence of charged and/or polar groups, graft copolymers according to the invention can be mixed with a higher amount of drugs with positively charged groups than neutral carriers can. Under application conditions an active drug is released more slowly by a material according to the invention than by a material without anionic groups.

Aiming at a pharmaceutical use of graft copolymers according to the invention, it should be noted that they are largely bio-degradable because polymers from hydroxycarboxylic acids like lactic and/or glycolic acid are hydrolyzed in the patient's body to lactic and/or glycolic acid, which are further metabolized to $CO_2$ and water. Graft copolymers according to the invention are therefore particularly advantageous for the production of parenterally applicable preparations. Variations in the structure can be used to modify the rate of degradation of the graft polymers according to this invention.

Graft copolymers according to the invention can be applied in all industrial areas that refer to polymers. They are especially useful as components of drug delivery systems allowing formulations of pharmaceutically active ingredients, especially for providing slow-release forms of drug delivery systems which can be used e.g. for parenteral or mucosal applications.

Graft copolymers according to the invention exhibit a core-corona structure with the negatively charged hydrophilic sulfonic groups oriented towards the outer aqueous phase which provides an optimal surface for the loading of cationic substances. This structure allows the preparation of colloidal carriers without the use of additional surfactants. This is extremely important for pulmonary applications, as the inhalation of significant amounts of surfactant may disturb the naturally regulated surface tension of the pulmonary lining fluid, thus leading to impaired lung function or inflammation.

SUMMARY OF THE INVENTION

As already stated above, the present invention provides graft copolymers of poly(vinyl sulfonic-co-vinyl alcohol)-g-poly(lactide-co-glycolide) (P(VS-VA)-g-PLGA) with negatively charged electrolyte properties.

A further solution to the underlying problem and thus a second aspect of the invention is a method of the synthesis of a graft copolymer according to the invention. This second aspect allows diverse modifications of the polymer's properties.

Further aspects of the present invention are
  A colloidal drug carrier, comprising a graft copolymer according to the invention;
  nanoparticles comprising a graft copolymer according to the invention as well as methods to synthesize them;
  a composition comprising (a) a biologically and/or pharmaceutically active drug and (b) a graft copolymer according to or synthesized according to the invention, a colloidal drug carrier or nanoparticles according to or synthesized according to the invention;
  the use of a graft copolymer according to the invention for the preparation of a colloidal drug carrier; and
  the use of a graft copolymer according to or synthesized according to the invention, a colloidal drug carrier or nanoparticles according to or synthesized according to the invention for the preparation of a composition comprising a biologically and/or pharmaceutically active drug for the controlled release of said drug.

These are described in detail in the text below and by reference to the following figures.

DETAILED DESCRIPTION OF THE PRESENT INVENTION

Figure 1:
FIG. 1: A typical reaction scheme for the synthesis of a graft copolymer according to the invention (see example 1).
Figure 1:
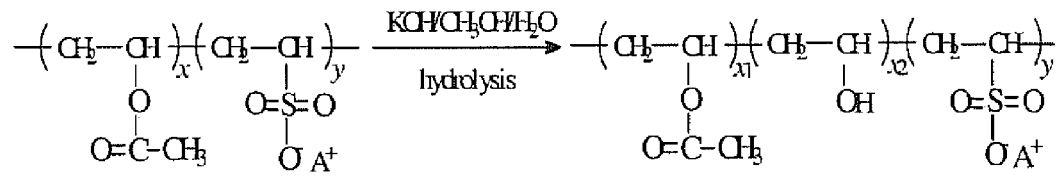
Figure 1:
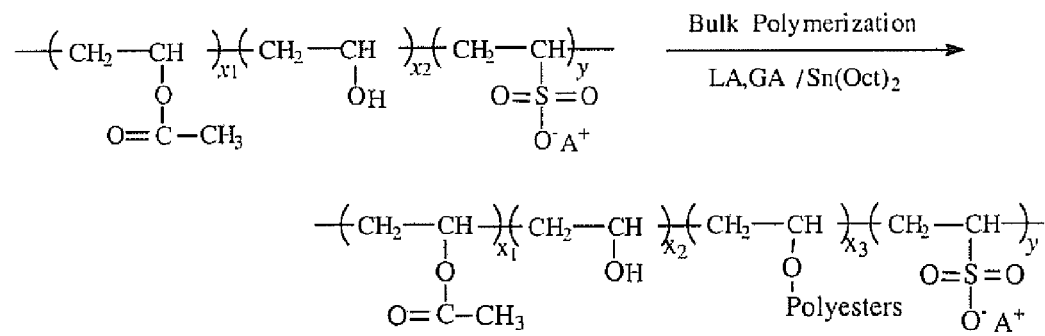
Figure 1:
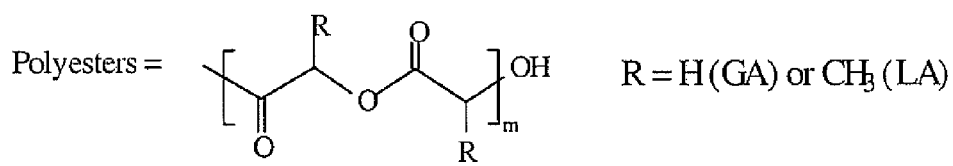

Unless otherwise defined, all technical and scientific terms used herein have the same meaning as those commonly understood by one of ordinary skill in the art to which the invention pertains.

All values and concentrations presented herein are subject to inherent variations acceptable in biological science within an error of ±10%. The term "about" also refers to this acceptable variation.

Graft polymers in the sense of the present invention are defined as polymers that comprise a polymeric backbone and grafted thereon (i.e. covalently bound) sidechains that themselves can be oligo- or polymers. Furthermore, the grafted parts of such a polymer can comprise a single type of monomers or a mixture of more than just one type of monomers.

Graft copolymers are defined as a certain group of graft polymers with a backbone that is not derived from a single type of monomers but from a mixture of more than just one type of monomers. Again, the grafted parts of such a polymer can also comprise a single type of monomers or a mixture of more than just one type of monomers.

In this sense the wording of poly(vinyl sulfonic-co-vinyl alcohol)-g-poly(lactide-co-glycolide) represents a graft copolymer comprising a copolymeric backbone derived from vinyl sulfonic (VS) and vinyl acetate (VAc), and grafted (g) thereon copolymeric side chains derived from a copolymerization of lactic acid (LA) and glycolic acid (GA). This is reflected by the abbreviation P(VS-VA)-g-PLGA.

The following nomenclature will be used to characterize graft copolymers according to the invention: P(VS-VA)-g-PLGA, or to describe the architecture of the diverse elements more precisely: P(VS-VA)-g-PLGA(X-Y), with the following meaning:
P: poly;
VS: vinyl sulfonic;
VA: vinyl alcohol;
VAc: vinyl acetate;
g: graft;
LA: lactic acid;
GA: glycolic acid;
PLGA: Polymer, derived from lactic and glycolic acid; because of its chemical structure it can also be defined as a certain "polyester" (see below).
X: The first number (X) in parenthesis designates the molar feed ratio of VS in the copolymerization. E.g., 2, 4, 6 and 8 represent the molar feed ratio of vinyl sulfonic of 20%, 40%, 60% and 80%, corresponding to the molar feed ratio of vinyl acetate of 80%, 60%, 40% and 20%.
Y: The second number (Y) in parenthesis designates the weight feed ratio of backbone vs. grafted polyester chains (P(VS-VA):PLGA), i.e. a feed ratio of 1:5 is denoted as Y=5, in general the weight feed ratio is 1:Y.

Graft polymers according to the invention are particularly useful in the technical field of drug delivery. They can also be described as "polymeric excipients". Other appropriate names to describe this use are "carriers" or "matrices". All these terms describe the use of this material to be mixed with one or more biologically and/or pharmacologically active drugs and optionally other ingredients in order to prepare a composition for a medical application. Such compositions can in principal be applied in any appropriate form, e.g. mucosal or parenteral.

The certain effect exerted by this material is a controlled and/or sustained release effect which is due to the physico-chemical properties of this material, especially due to the possibility of electrostatic interactions of this material with the admixed drugs and to the hydrolysis rate of the graft copolymer.

The overall electrolyte properties of the graft copolymer according to the invention can be described as negatively charged electrolyte properties. As required by the underlying problem the polymers according to the invention have to allow effective loading and sustained-release of positively charged drugs, proteins and peptides. This is solved by this feature of overall negatively charged electrolyte properties. However, within the same polymer molecule variations in the distribution of charged groups, even leading to partially positively charged areas might exist which might be useful for certain applications and are therefore comprised by this invention as well.

For example a variation of the degree of negatively charged groups of the backbone can be used to optimize this system for different biologically active molecules to be associated with such a carrier system. For example a graft copolymer according to the invention with a high amount of negatively charged groups can be used especially for positively charged low molecular weight molecules.

A variation of the hydrolyzable polyester side chains can be used for an accommodation of the hydrolysis rate and thus of the drug release when the final preparation is applied to a patient.

The hydrophilicity of the polymer according to the invention is influenced by the polarity of the polyester side chains and especially influenced by the negative charge of the functional groups of the backbone. Therefore, by changing the number or length of the PLGA side chains or by changing the number of negatively charged substituents, i.e. the VS, the hydrophilicity can also be changed. Also, the hydrophilicity changes with differing chain length of the PLGA side chain, and with the relative amount present in the polymer.

Charged pharmacologically active substances are bound primarily by electrostatic interaction; lipophilic substances can be adsorbed to or dissolved in the polymer matrix. The hydro- and the lipophilic properties of the polymer matrix can be adjusted by the graft degree of the P(VS-VA) backbone with PLGA chains. The charge properties can be modified by variation of the amount of charged vinyl sulfonic groups in the P(VS-VA) backbone.

The solubility properties can be modified by the following principle: Short PLGA side-chain length and high degree of sulfonic substitution result in more hydrophilic and water soluble polyesters, whereas polyesters with long side chains and low degree of sulfonic substitution show a more lipophilic nature.

The graft copolymers according to the invention are generally highly biodegradable by hydrolysis, which is especially due to the hydrolyzable polyester side chains. The kinetics of biodegradation will depend, among other factors such as size of the polymeric particle or physiological environment (e.g. the pH value) which are known to the person skilled in the art, on hydrophilicity of the polymer. In contrast to conventional single chain polyesters where degradation occurs by random scission of the long polyester chain, the comb-like structure of the copolymers according to the invention allows for many more moieties for hydrolytic attack on the side chains. The possibility to modify hydrophilicity using the sulfonic substitution will also influence the rate of biodegradation. Furthermore, the graft copolymers according to the invention can exhibit an acidic microenvironment due to the presence of the sulfonic groups, further increasing the rate of acid hydrolysis of the polyester.

Due to the high amount of charged and/or polar groups, graft copolymers according to the invention can form colloidal micro- or nanoparticles. Such particles with a typical size between 50 nm and 500 nm (which range is not intended to limit the scope of the claims) are especially well suited as drug carriers for parenteral and for mucosal applications (see below).

Graft copolymers according to the invention can be synthesized through methods which are in principle known to the person skilled in the art. Certain ways for the synthesis, which might also be interpreted as starting points for further variations are described below and illustrated by the examples.

A preferred graft copolymer according to the invention is described by this formula (I):

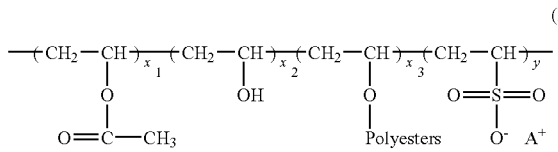

wherein
$A^+$ is selected from $Na^+$, $K^+$, $Li^+$, $NH_4^+$, or any other monovalent cation,
the number of monomer units (x1+x2+x3+y) is equal or below 1 000,
the mol ratio (x1+x2+x3) vs. y is from 0.1 to 10,
the mol ratio x2 vs. x3 is from 0 to 0.1,
the mol ratio x1 vs. x3 is from 0 to 0.1, and
"Polyesters" is a random homo- or co-polymer described by this formula (II):

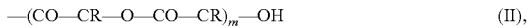

wherein
R is H or $CH_3$, and
m is an integer from 1 to 100.

A graft copolymer according to the invention comprises a backbone which is composed of different monomer units with certain substituents. That backbone is preferably produced by a copolymerization process of both monomers, which process is in principle known for a person skilled in the art. E.g. in example 1 a radical copolymerization process is described for the synthesis of the backbone.

The substituents of the backbone are acetyl, hydroxyl, "polyester" and sulfonic groups. Each of these groups can be present in different amounts, as expressed by the indices x1, x2, x3, y, respectively. The monomer units with the acetyl, hydroxyl, and "polyester" groups as substituents (x1, x2, x3) can all be derived from one acetyl group, through partial hydrolysis and subsequent grafting, as exemplified in example 1 and FIG. 1. Accordingly, x1, x2, x3 in the final product sum up to the number of x, which has been used to describe the amount of VAc during the initial reaction of the synthesis of the backbone.

It should also be noted that the composition of the backbone as well the composition of the side chains is in principle random. There is no stringent order of alternate VA and VS groups in the backbone after its initial synthesis because the polymerization process is random. There is also no stringent order of acetyl, hydroxyl, and polyester groups in the grafted copolymer according to the invention because the hydrolysis of the acetyl side chains (e.g. in reaction step (b); see FIG. 1) is also in principle random. Furthermore the grafting reaction does not take necessarily place at all free hydroxyl groups of the non-grafted copolymer.

Thus, x (as the sum of x1 and x2 and x3) characterizes the number of the vinyl acetate derived monomer units in the backbone after its formation.

y characterizes the number of the vinyl sulfonic derived monomer units in the backbone after its formation.

The values of x and y can be controlled via the polymerization reaction conditions, as known in principle by a person skilled in the art and as outlined below and illustrated by the examples. The total sum, however, of these monomer units can especially be controlled via the amounts of the feed of the respective monomers VAc and VS at the beginning of the synthesis of the backbone, and in general by the reaction conditions.

Results of alternative and/or obviously modified processes are also comprised by the invention.

As illustrated by the reaction scheme in FIG. 1, part B, a graft copolymer according to the invention comprises a backbone which is further modified within the vinyl acetate/vinyl sulfonic-derived repeating unit. Especially through a hydrolysis step a subset of the vinyl acetate derived monomer in the backbone is hydrolyzed to result in a free hydroxyl group. This transformation can be controlled via the reaction conditions, as known in principle by a person skilled in the art and as outlined below and illustrated by the examples. Results of alternative and/or obviously modified processes are also comprised by the invention.

$x_1$ then represents the number of the not hydrolyzed vinyl acetate derived monomer in the backbone, and $x_2$ represents the number of the hydrolyzed vinyl acetate derived monomer in the backbone.

The grafting reaction is also per se known to a person skilled in the art and also exemplified by FIG. 1 and example 1. Alternatives and variations to these processes are possible, especially in order to vary the variables and m.

As can be seen e.g. from the reaction scheme in FIG. 1, part C, a polymer according to the invention further comprises grafted side chains derived from a copolymerization of lactic acid (LA) and glycolic acid (GA). These are bound via the hydroxyl group, derived from the partial hydrolysis of the vinyl acetate derived monomer in the backbone. Accordingly, the number of "polyester" side chains is due to the value of $x_2$, as defined above and of the efficiency of the grafting reaction. This grafting reaction can be controlled via the polymerization reaction conditions, as known in principle by a person skilled in the art and as outlined below and illustrated by the examples. Results of alternative and/or obviously modified processes are also comprised by the invention.

Again, the grafting reaction is in principle random. LA and GA derived monomer units are not ordered in a stringent order but statistically. This explains why the substituent R can (in most cases) not be explained more precisely. R represents the respective remaining parts of the molecules lactic acid (LA) and of glycolic acid (GA) which are —$CH_3$ and —H, respectively. Over the total stretch of the "polyester" side chain described in formula (II), there is a statistical order of —$CH_3$ and —H substituents which order is due to the statistical polymerization process of both monomers. The total sum, however, of these substituents can especially be controlled via the amounts of the feed of the respective monomers. Results of alternative and/or obviously modified processes are also comprised by the invention.

Thus, m characterizes the number of the LA and GA derived monomer units in the PLGA side chain, as illustrated by formula (II).

The value of m can be controlled via the polymerization reaction conditions, as known in principle by a person skilled in the art and as outlined below and illustrated by the examples. Results of alternative and/or obviously modified processes are also comprised by the invention.

In typical cases the weight ratio of P(VS-VA):PLGA is chosen as 1:5, 1:10, 1:15 or any other ratio between these values or even lower or higher. This ratio can especially be controlled via the reaction conditions during the feed in the grafting reaction, as illustrated by the examples of this application.

A variation of this ratio changes e.g. the overall physicochemical properties of the resulting material like hydrophilicity, biodegradation rates and loading properties of the polymer. As illustrated by the accompanying examples an increase of this ratio leads to an increase of the glass transition temperature. Also, the ability to form colloidal nanostructures will be affected by a change of the weight ratio. For example, a high proportion of the P(VS-VA) backbone will increase hydrophilicity, and will enhance water uptake by nanoparticles derived from such polymer.

As evidenced by the data presented in the examples, especially in example 7, the analyzed variations of the synthesis method according to the invention allow the production of graft polymers with diverse physicochemical properties. This proves that by this invention a group of related polymers with definitively variable properties is made available.

As further evidenced by the data presented in the examples, especially in example 8, variations in the synthesis lead to variations in the polymer leading to different nanoparticle properties, thus making the graft copolymers according to the invention well suitable to tailor the characteristics needed for a polymeric drug delivery system.

A further component of formula (I) is $A^+$. This component represents any monovalent cation as counterion to the sulfonic group of the backbone of a graft polymer according to the invention. The ions $Na^+$, $K^+$, $Li^+$, $NH_4^+$, especially $Na^+$ are mostly preferred. It should be kept in mind that at least a small degree of the sulfonic groups of the backbone might stay in protonated i.e. acid form, which is especially due to the chemical equilibrium between the protonated and deprotonated acidic groups and remaining water molecules in close contact to the polymers according to the invention. However, the overall electrolyte properties of the polymers according to the invention are described as an overall negative charge, which is due to the non-protonated sulfonic groups and the respective counterions.

With respect to the envisaged application of the graft copolymer it is advisable to limit the total number of monomer units $(x1+x2+x3+y)$ to a value of 1 000 or below.

The molecular weight (MW) of the total graft copolymer results from the backbone component as well as from the PLGA side chains. The molecular weight of the backbone component alone can be calculated by analysis of the product of step (b) according to the reaction scheme as shown in FIG. 1, i.e. after polymerisation of VS and VAc and subsequent (at least partial) hydrolysis of the acetyl groups, derived from VAc.

In preferred graft copolymers according to the invention the MW of backbone component is below 50 000 Da. More preferred are values below 20 000 Da and even more preferred 2 000 to 8 000 Da. This is especially due to the intended use of such copolymers for medical applications. In this case the copolymer is absorbed by the patient's body and the resulting metabolites have to be secreted, mostly via the kidneys. The complete copolymer can be hydrolyzed, especially with respect to the grafted polyester components. However, the backbone comprises C—C bonds which cannot be hydrolyzed effectively by the body of a mammal. This means that large parts of the backbone remain to be secreted via the kidneys. Therefore the MW of the backbone has to be limited, preferably to the above designated values.

In typical cases the contribution of the grafted side chains to the total MW of the graft copolymer is higher than the one from the backbone. As mentioned above the weight ratio of P(VS-VA):PLGA is preferably chosen as 1:5, 1:10, 1:15 or even higher. Which means that the total MW of the graft copolymer can be many times higher than the contribution of the backbone alone.

Because the side chains can be hydrolyzed by a mammal's, especially the human body, such a large MW is not expected to cause severe problems for the metabolization of the complete graft copolymer.

According to the invention the mol ratio $(x1+x2+x3)$ vs. $y$ is from 0.1 to 10. Such a wide variation of the VAc and VS derived monomers allows a wide variation of the chemical and physicochemical properties of the resulting graft copolymer. A high amount of $(x1+x2+x3)$ allows a wide variation with respect to the grafting reaction. The amount of $y$ allows a wide variation of the surface charge of the polymer and thus its applicability as a polymeric excipient for diverse molecules. Such a wide variation is not possible when e.g. a definite backbone like polyoxyethylene or dextran is used. Also sulfobutyl polyvinylalcohol grafted with PLGA (SB-PVAL-g-PLGA) does not allow such a wide variation of the distribution of negative charges over the complete polymer.

According to the invention the mol ratio $x2$ vs. $x3$ is from 0 to 0.1. This value describes the extent of the grafting with the polyester side chains and can be used to vary especially the hydrophilicity and the overall structure of the grafted copolymer according to the invention.

According to the invention the mol ratio $x1$ vs. $x3$ is from 0 to 0.1. This value describes the extent of the grafting with the polyester side chains in comparison to the side chains still remaining from the initial VAc monomers of the backbone synthesis. A variation of this value can also be used to vary especially the hydrophilicity and the overall structure of the grafted copolymer according to the invention.

According to the invention $m$ is an integer from 1 to 100. This variable characterizes the length of the PLGA side chain. This can also be varied in order to affect the hydrophilicity and the overall structure of the grafted copolymer according to the invention. Additionally a variation of this value can be used to accommodate the hydrolysis rate of the grafted copolymer which in turn will influence the release of an admixed substance as well as the biodegradability.

In view of a medical application it is desired in many cases to sustain the release of an admixed substance in comparison to the release of the same substance not admixed to a drug delivery system. This effect can very efficiently be controlled via the characteristics of the polymer and the drug delivery system, e.g. by particle size of the carrier, hydrophilicity, zeta potential and hydrolysis characteristics of a polymeric excipient according to the invention, all of which are accessible for variation by the polymer composition.

Thus, a sustained release effect can not only be reached but also be controlled and finely tuned through the design of the admixed copolymer according to the invention.

All variations of these ratios lead to a very high flexibility in designing a large number of related graft copolymers according to the invention which allows the design of very specific polymers for a multitude of different effects vs. hydrophilicity-hydrophobicity, release rates and biodegradation when applied, especially for medical uses.

A further preferred embodiment of the invention comprises a graft copolymer according to the invention, wherein $A^+$ is selected from $Na^+$ or $K^+$, preferably $Na^+$.

It is desired to introduce a negative charge via the respective sulfonic group. Therefore it is advisable to use a strong counterion for the sulfonic group. Further, as seen from example 1 the vinyl sulfonic acid sodium salt turned out to be a very convenient and efficient reaction partner for the synthesis of the backbone of the polymer.

A further preferred embodiment of the invention comprises a graft copolymer according to the invention, wherein the number of monomer units (x1+x2+x3+y) is equal to or below 300, preferably from 20 to 100.

This size range seems to be very promising for several applications of the respective copolymer, especially for a desired medical use.

A further preferred embodiment of the invention comprises a graft copolymer according to the invention, wherein the mol ratio (x1+x2+x3) vs. y is from 0.2 to 5, preferably from 0.5 to 1.

This size range seems to be very promising for several applications of the respective copolymer, especially for a desired medical use.

A further preferred embodiment of the invention comprises a graft copolymer according to the invention, wherein the mol ratio x2 vs. x3 is from 0 to 0.05, preferably from 0 to 0.01.

This means that there are much less unsubstituted hydroxyl groups in the final polymer than grafted side chains. However, these ranges seem to be very efficient for the modification of the hydrophilicity of the complete molecule, especially in view of its possibility to form colloids and nanoparticles as described below.

A further preferred embodiment of the invention comprises a graft copolymer according to the invention, wherein the mol ratio x1 vs. x3 is from 0 to 0.05, preferably from 0 to 0.01.

This size range seems to be very promising for several applications of the respective copolymer, especially for a desired medical use.

A further preferred embodiment of the invention comprises a graft copolymer according to the invention, wherein the mol weight ratio of the backbone poly(vinyl sulfonic-co-vinyl alcohol), consisting of all groups x1 and x2 and x3 without "Polyesters" and y according to formula (I), vs. graft PLGA, consisting of all groups "Polyesters" according to formulae (I) and (II), (expressed as P(VS-VA):PLGA) is between 1:2 and 1:30, preferably between 1:3 and 1:20, more preferred between 1:5 and 1:15, even more preferred between 1:8 and 1:12 and mostly preferred 1:10.

This size range seems to be very promising for several applications of the respective copolymer, especially for a desired medical use which requires an individual fine tuning of the respective effects of both parts of the molecule, especially the hydrophilicity of the grafted side chains and the polarity and charge distribution of the backbone.

A further preferred embodiment of the invention comprises a graft copolymer according to the invention, wherein m is an integer from 5 to 60, preferably from 10 to 30.

By this size range it is possible to control the overall hydrolysis rate and the hydrophilicity of the polymer. This size range seems to be very promising for several applications of the respective copolymer, especially for a desired medical use.

A further preferred embodiment of the invention comprises a graft copolymer according to the invention, wherein the mol ratio of LA (R=$CH_3$) vs. GA (R=H) is between 0 to 100 and 100 to 0, preferably between 1 to 99 and 99 to 1, more preferred between 10 to 90 and 90 to 10, even more preferred between 30 to 70 and 70 to 30, mostly preferred between 45 to 55 and 55 to 45.

This variation also allows a modification of the hydrophobicity of the graft copolymer and can be varied especially in respect to the admixture with molecules that are characterized by different values of hydrophilicity/hydrophobicity.

A further preferred embodiment of the invention comprises a graft copolymer according to the invention that is characterized by a glass transition temperature ($T_g$) between 10 and 50° C., preferably between 20 and 40° C., mostly preferred between 25 and 38° C.

This parameter describes the random structure of the copolymer. This size range seems to be very promising for several applications of the respective copolymer, especially for a desired medical use. This use requires the optimal admixture with the intended drug and thus the physical handling of both components must be reached in a certain temperature range where both are mixed with each other. These values and how they can be modified is exemplified by example 6 of this application.

In principle the same applies to the physicochemical parameter of the intrinsic viscosity, or inherent viscosity (limiting viscosity number; Staudinger index) as a parameter, accepted by the IUPAC to describe especially polymers. It is given in dl/g=$cm^3/g^{-1}$. A further preferred embodiment of the invention comprises a graft copolymer according to the invention that is characterized by having an intrinsic viscosity between 0.01 and 1.0, preferably between 0.02 and 0.2, mostly preferred between 0.04 and 0.18 dl/g.

These values and how they can be modified is exemplified by example 2 of this application.

A further preferred embodiment of the invention comprises a graft copolymer according to the invention that is characterized by a 50% degradation time between 2 and 28 days, preferably between 2 and 18 days, more preferred between 2 and 10 days, measured under the following conditions:
a) capture of a polymer film from a 5% (w/v) solution of the graft copolymer according to the invention in dichloromethane, resulting in a set of equal samples to be treated in the following steps;
b) drying for 72 h at a temperature of 4° C.;
c) removal of residual solvents in vacuo at 25° C. until constant weight;
d) incubation in 0.15 M phosphate buffered saline (PBS), pH 7.4, at 37° C. and gentle shaking once a day;
e) recovering of samples at several points in time during the monitored time course;
f) freeze drying of the recovered samples for ca. 72 h in vacuo at 25° C. until the reach of a constant mass;
g) and the following calculation:
Mass loss (%)=100−(mass (dry)×100/original mass), with:
mass (dry)=weight after step (f) and
original mass=weight after step (c).

The measurement of this parameter is exemplified by example 7 of this application. It is further illustrated by FIG. 8. In this figure the value of 50% remaining mass is shown by a dotted line.

This parameter describes the stability of the copolymers in a model designed to resemble in vivo conditions after the administration of a pharmaceutical comprising a copolymer according to the invention. It is desirable to find an equilibrium between stability during the storage of the respective preparation and the release rate under application conditions. As explained above, also that release should in most cases not take place immediately but sustained during a certain time interval. The defined values are found to meet this requirement best, especially for a desired medical use.

A further preferred embodiment of the invention comprises a graft copolymer according to the invention that is characterized by the ability of forming nanoparticles with a mean particle size between 50 and 500 nm, preferably between 100 and 250 nm, more preferred between 120 and 160 nm.

The terms microparticles and nanoparticles refer to the size of the respective particles. In this respect the state of the art is not always consistent; e.g. a group of particles with a medium size of 500 nm—and thus particles in the "nano"-range—statistically also comprises in most cases some particles of 800, 900 or even 1 000 nm and can thus also be seen als "micro"-particles. Therefore, according to the invention all small particles below 1 mm medium size are named nanoparticles. However, preferred are the above mentioned size ranges which are always applicable to the mean particle size.

This ability is largely due to the hydrophilicity properties of the respective graft copolymer, but also to other physico-chemical properties. To test this ability for a certain graft copolymer a reaction like the one which is described in example B can be performed.

These preferred size ranges seem to be very promising for several applications of the respective copolymer, especially for a desired medical use as they take into account the necessity of preparing them as well as the storage stability and the ability of the patient's body to resorb such particles.

The present invention provides a method of the synthesis of a graft copolymer of poly(vinyl sulfonic-co-vinyl alcohol)-g-poly(lactide-co-glycolide) (P(VS-VA)-g-PLGA) with negatively charged electrolyte properties, comprising the steps of:
a) synthesis of a polyelectrolyte backbone by radical copolymerization of vinyl acetate and a vinylsulfonic acid salt in the presence of a polar solvent and a catalyst, optionally followed by isolation and/or purification and/or drying of the product,
b) complete or partial hydrolysis or alcoholysis of poly(vinylsulfonic-co-vinylacetate) (product of (a)) under alkaline conditions in the presence of a solvent, optionally followed by isolation and/or purification and/or drying of the product and,
c) grafting of poly(lactide-co-glycolide) (PLGA) to the sulfonic modified poly(vinyl alcohol) (product of b) through ring-opening polymerization in the presence of a catalyst, optionally followed by isolation and/or purification and/or drying of the product.

These steps have already been outlined above in the context of the description of the polymer according to the invention. Further means for controlling the reaction steps and variations are summarized in the following.

In step (a) vinyl acetate and vinylsulfonic acid in the form of its salt, preferably in the form of a salt with a monovalent cation, mostly preferred in the form of its sodium salt, are copolymerized. Appropriate polar solvents can be e.g. water and/or an alcohol like methanol. The copolymerization reaction is carried out via the radical polymerization process. Appropriate initiators of the copolymerization reaction are for example ammonium persulfate ($(NH_4)_2S_2O_8$; APS, water soluble), 2-(Biphenyl-4-yl)-5-phenyloxazol (BPO) or Azo-bis-isobutyro-nitril (AIBN), all generally known as appropriate initiators for the radical polymerization of vinyl acetate. The most preferred initiator is APS.

However, the solvent system has to be chosen with respect to the solubility of the reaction components. For example, vinyl acetate can not be dissolved in water, but in a mixture of methanol and water. On the other hand, vinyl sulfonic sodium is preferably supplied as an aqueous solution, preferably as a 30% aqueous solution. Accordingly, the amount of methanol in a methanol/water mixture is to be chosen in relation to the amount of vinyl acetate.

BPO and AIBN are substantially insoluble in water, while APS is insoluble in pure methanol but soluble in water. For this reason the mostly preferred solvent is also a mixture of water/methanol, preferably at a v/v-ratio of 0.2 to 5.

For radical polymerization, especially the purity of each monomer, the kind of the initiator, the solvent and the polymerization temperature have significant effects on the molecular weight of obtained product. The degree of polymerization can be controlled by the amount of initiator in the system. During the polymerization of vinyl acetate, the chain transfer reaction to the solvent takes place easily because of the high reactivity of vinyl acetate. Therefore, the polymer composition will not directly reflect the feed ratio but has to be adapted experimentally, which is in principle known to a skilled person.

The copolymerisation reaction should take place below the boiling points of vinyl acetate (72° C.) and methanol (63-64° C.). A preferred range is 55-65° C., most preferred is about 60° C.

Further it has been proven to be useful to perform a refluxing reaction under a protection gas like nitrogen or argon.

The unreacted vinyl acetate can be eliminated by evaporation in methanol after polymerization. The unreacted vinyl sulfonic sodium and other small molecular weight impurities, some produced by hydrolysis, can be eliminated by a subsequent ultrafiltration, all of which are in principle known to a person skilled in the art.

In reaction step (b), the hydrolysis or alcoholysis step, the product of step (a) is brought into contact with water and/or an alcohol like ethanol under alkaline conditions. These conditions are chosen to allow a reaction of at least some of the vinylacetate side chains of the poly(vinylsulfonic-co-vinylacetate), resulting from step (a). According to the invention a complete or partial hydrolysis and/or alcoholysis will change this reacting proportion (x2) of the vinylacetate side chains into hydroxyl groups. The remaining, not hydrolyzed or alcoholyzed proportion is expressed as x1.

In the hydrolysis reaction, the amount of KOH in relation to VAc units can be used to control the degree of hydrolysis. For a complete hydrolysis (e.g. according to example 2) a conventional amount of KOH used can be 0.3 to 0.5 mole ratio to VAc units in the backbone.

Reaction step (c) can be described as a bulk polymerization as well as the grafting reaction. In this step the product of step (b), which can be described as a sulfonic modified poly(vinyl alcohol), characterized by a number (x2) of hydroxyl groups, is brought into contact with monomers of lactic acid/glycolic acid (see below) in the presence of an appropriate catalyst. These reaction conditions are chosen to allow a polymerization reaction of these monomers with/onto the hydroxyl groups of the backbone which have been prepared through step (b). This grafting reaction can be carried out in solution or preferably without the presence of a solvent (compare example 1) and can then be described as a melt polymerization. It leads to a polymer, comprising a sulfonic modified poly(vinyl alcohol) backbone which is grafted with poly(lactide-co-glycolide).

As known from the state of the art glycolic acid (OH—$CH_2$—COOH) and lactic acid ($CH_3$—C*H(OH)—COOH) can dimerize to form a cyclic lactone of this formula:

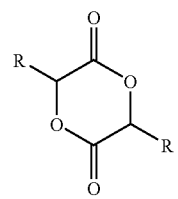

$R = H; CH_3$

These molecules can be subjected to a ring opening polymerization when Lewis acids are present as catalysts. For example, a grafting of such a PLGA polymer, comprising repeating units of opened rings of these lactones onto a dextran backbone is described in Li et al. (1997); *Polymer*, vol. 38, pages 6197-6206.

Accordingly, step (c) of a method of the synthesis of a graft copolymer according to the invention is also described as a ring opening polymerization reaction. Since the ring opening polymerization starts in preferred embodiments of the invention from dimeric monomer units, the PLGA side chains will in principle contain two lactic acid or two glycolic acid monomer units consecutively, as is also illustrated by formula (II). Deviations from this ordering are possible in principle in small quantities (e.g. from heterodimers that may form in situ during the polymerization reaction), depending on the reaction conditions.

Appropriate catalysts of the step (c) reaction are Lewis acids, preferably stannous octoate ($Sn(Oct)_2$).

Optionally and in order to finish each of these steps (a), (b) and (c) as many steps as required can be added for properly isolation, purification and/or drying of the respective product. This depends especially on the requirements of the subsequent step or the intended use of the final product. If for example step (c) is carried out as a melt polymerization any solvent from the foregoing steps has to be eliminated. Also the final product of step (c) must fulfill certain purity requirements in respect to the envisaged use. Such isolation, purification and/or drying steps of the respective product are in principle known to the person skilled in the art and can be applied in any appropriate mode. This is also illustrated by the examples.

After each of these steps (a), (b) and (c) of the synthesis the respective resulting polymers can be characterized by techniques known in the state of the art. For example the result of step (a), the P(VS-VA), can be characterized by FT-IR, $^1H$ NMR, DSC, GPC, intrinsic viscosity, elemental analysis (Sulfur), $^{13}C$ NMR or by any other method known to the skilled person that seems to be appropriate. The result of step (c), the P(VS-VA)-g-PLGA can e.g. be characterized by elemental analysis (Sulfur), FT-IR, $^1H$ NMR to determine PLGA units per chain), $^{13}C$ NMR, intrinsic viscosity, DSC or by any other method known to the skilled person that seems to be appropriate.

For example $^1H$ NMR spectra can be used to calculate the side length of the PLGA of the polymers according to the invention (see examples 5 and 6).

DSC analysis can be used for the determination of the glass transition temperature ($T_g$) (see example 6).

For example GPC analysis can be used to determine the $M_w$ value as well as the $M_n$ value of the polymer. $M_w$ is defined as the weight-average molecular weight whereas $M_n$ is defined as the molecular weight averaged over the total number of molecules.

A typical reaction scheme for the synthesis of a polyester according to the invention is shown in FIG. 1. A possible preparation method is described in example 1. Both are mentioned here only for illustration purposes and without limiting the scope of protection in any respect.

As evidenced by the examples of this application the present invention provides a facile method for the introduction of sulfonic substitution group in an amphiphilic polyester.

The amphiphilic and negatively charged nature of the grafted polyesters allows drug entrapment by electrostatic interaction as a function of sulfonic modification and can be used as negatively charged polyelectrolyte platform for drug delivery.

Additionally, the sulfonic-modified charge ratios of the backbone and the side lengths of PLGA can be modified to adjust the amphiphilic nature and the solubility of the polymers. This provides an approach to engineer the resulting particle surface properties using P(VS-VA)-g-PLGA with different degrees of sulfonic substitution and PLGA chain lengths.

In order to obtain different sulfonic substituted backbones, the feeding of monomer ratios of vinyl sulfonic and vinyl acetate can be varied. They can be chosen for example as 2:8, 4:6, 6:4, and 8:2 VS vs. VAc (as outlined in the examples) or any other ratio between these values or even lower or higher in order to modify and control the composition of the backbone, influencing polyelectrolyte and degradation properties. In detail these variations influence the amount of negative charges on the final polymer and the rate of its degradation due to hydrolysis when applied e.g. to a patient. Both values amount up to 10, which allows a precise definition through giving just the first value (compare example 2 and FIG. 2).

For example, from the intrinsic intrinsic viscosity data in table 1 it can be seen that the increasing of VS:VA ratio in the backbone leads to decreasing intrinsic viscosity of the resulting polymer. This is an indicator that the function of sulfonic modification increases the hydrophilicity of the backbone.

The result of esp. example 6 proves that the variations of the synthesis method according to the invention allow the production of graft polymers with diverse physicochemical properties. Thus the invention provides a group of related polymers with definitively variable properties and subtle differences which are especially useful for the above mentioned medical purposes.

Preferred embodiments of this aspect of the invention, already outlined by the description above can be summarized as follows:

A method of the synthesis of a graft copolymer according to the invention with a polar solvent in step (a), preferably one that is selected from water, methanol, ethanol and/or isopropanol, more preferred a mixture of methanol and water;

a method of the synthesis of a graft copolymer according to the invention with a radical polymerization initiator as catalyst in step (a), preferably APS;

a method of the synthesis of a graft copolymer according to the invention with $KOH/CH_3CH_2OH/H_2O$ or $NaOH/CH_3CH_2OH/H_2O$ as reagents in step (b);

a method of the synthesis of a graft copolymer according to the invention with stannous octoate ($Sn(Oct)_2$) as catalyst in step (c).

These embodiments are exemplified by example 1 and the following examples and turned out to be especially useful for the synthesis of a graft copolymer according to the invention.

Based on the same experiences the following combination of features characterizes a very preferred embodiment of the invention; this is a method of the synthesis of a graft copolymer according to the invention comprising the steps of:

a) Radical copolymerization of vinyl sulfonic acid sodium and vinyl acetate, according to the following reaction scheme:

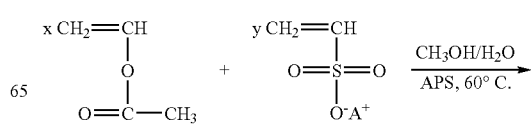

-continued $$-\!\!-\!\!(CH_2-CH)_x\!\!-\!\!(CH_2-CH)_y\!\!-\!\!,$$
with pendant O—C(=O)—CH$_3$ and O=S(=O)—O$^-$A$^+$ groups b) Hydrolysis to obtain poly(vinyl sulfonic-co-vinyl alcohol), according to the following reaction scheme:

$$-\!\!-\!\!(CH_2-CH)_x\!\!-\!\!(CH_2-CH)_y\!\!-\!\! \xrightarrow{\text{KOH/CH}_3\text{OH/H}_2\text{O}}_{\text{hydrolysis}}$$

$$-\!\!-\!\!(CH_2-CH)_{x1}\!\!-\!\!(CH_2-CH)_{x2}\!\!-\!\!(CH_2-CH)_y\!\!-\!\!,$$
with pendant O—C(=O)—CH$_3$, OH, and O=S(=O)—O$^-$A$^+$ groups and c) Graft PLGA(LA:GA=50:50), according to the following reaction scheme:

$$-\!\!(CH_2-CH)_{x1}\!\!(CH_2-CH)_{x2}\!\!(CH_2-CH)_y\!\! \xrightarrow[\text{LA,GA/Sn(Oct)}_2]{\text{Bulk Polymerization}}$$

$$-\!\!(CH_2-CH)_{x1}\!\!(CH_2-CH)_{x2}\!\!(CH_2-CH)_{x3}\!\!(CH_2-CH)_y\!\!-$$

with

Polyesters = 
$$\left[\begin{array}{c} R \\ \vert \\ \text{---CH---O---C---}\\ \vert\phantom{xxx}\vert \\ \phantom{xx}O \end{array}\right]_m \text{OH}$$

R = H (GA) or CH$_3$ (LA).

A preferred embodiment of this aspect of the invention is a method of the synthesis of a graft copolymer according to the invention with a monomer feeding ratio of vinyl sulfonic vs. vinyl acetate (VSA:VAc) in step (a) between 2:8 and 8:2, preferably between 4:6 and 6:4 mol %.

As described above this variation can be used to modify the physicochemical properties of the resulting graft copolymer. The effects of this variation as well as the success in producing polymers according to the invention by this process are described in example 2.

A preferred embodiment of this aspect of the invention is a method of the synthesis of a graft copolymer according to the invention with a graft monomer ratio of lactic acid vs. glycolic acid (LA:GA) in step (c) between 0 to 100 and 100 to 0, preferably between 1 to 99 and 99 to 1, more preferred between 10 to 90 and 90 to 10, even more preferred between 30 to 70 and 70 to 30, mostly preferred between 45 to 55 and 55 to 45.

As described above this variation can be used to modify the physicochemical properties, especially the hydrophilicity/hydrophobicity properties of the resulting graft copolymer within a wide range.

A preferred embodiment of this aspect of the invention is a method of the synthesis of a graft copolymer according to the invention with a backbone vs. graft weight ratio (P(VS-VA): PLGA) in the feed in step (c) between 1:2 and 1:30, preferably between 1:3 and 1:20, more preferred between 1:5 and 1:15, even more preferred between 1:8 and 1:12 and mostly preferred 1:10.

As described above this variation can be used to modify the physicochemical properties, especially the hydrolysis and bio-degradation properties of the resulting graft copolymer within a wide range.

As a further solution of the above described problem, the present invention provides a colloidal drug carrier, comprising a graft copolymer according to the invention.

In the sense of the current invention, drug carriers are substances defined by their activity. They serve as substances that improve the delivery and the effectiveness of drugs at their biological or pharmaceutical application. They can be applied in different drug delivery systems with the aim to control the release of the drug, influence the metabolism or the toxicity of the respective drug or to increase the effectiveness of drug delivery to the target sites of pharmacological actions. Also polymers can serve as a basis for drug carriers. Further components of a drug carrier can be other polymers, solvents like water, salts, tensides, liposomes, microspheres etc.

Due to the above described properties, a graft copolymer according to the invention can serve as a component in such a carrier system. Especially because of the hydrophophilicity of its backbone it can easily be complexed with solvents, especially water to build up a colloid, which in turn is extremely well suited for the design of drug carriers, especially for the use of positively charged drugs.

Preferred embodiments of this aspect of the invention are:
A colloidal drug carrier, comprising a graft copolymer, synthesized according to the present invention;
a colloidal drug carrier according to the invention, which is substantially free from surfactants.

The second aspect is extremely important for an envisaged medical application via mucous membranes, especially via the lung epithelia. Especially the formation of nanoparticles as described in example 8 is possible without the addition or use of surfactants or other excipients, so that these drug carriers are especially well suited for the envisaged application.

As a further solution of the above described problem, the present invention provides nanoparticles comprising a graft copolymer according to the invention with a mean particle size between 50 and 500 nm, preferably between 100 and 250 nm, more preferred between 120 and 160 nm.

As explained above such particles are well suited for the delivery of biologically and/or pharmaceutically active drugs. The preparation of such particles, starting from a graft copolymer according to the invention can in principle be carried out with the knowledge of a person skilled in the art. It is further exemplified by example 8.

In a preferred embodiment such nanoparticles are characterized by a polydispersity index between 0.05 and 0.1.

Particles within this relatively well defined size range are well suited for medical applications, especially in respect to the absorption and drug release properties.

Another preferred embodiment are nanoparticles according to the invention with a zeta-potential between −15 and −60 mV.

This parameter describes the surface charge of the respective particles. The negative value makes it well suited for the interaction with positively charged drugs. This certain range has turned out to be useful for drugs which are applied in medicine. Example 8 exemplifies how such particles can be synthesized.

Consequently, as a further solution of the above described problem, the present invention provides a method of the synthesis of nanoparticles according to the invention, comprising the steps of:
a) dissolving a graft copolymer according to the present invention and/or a graft copolymer synthesized according to the present invention in an organic solvent,
b) injecting the solution resulting from step (a) into an aqueous phase and
c) removing the organic solvent.

This method has turned out to be successful for the preparation of nanoparticles according to the invention.

In a preferred embodiment such a method is characterized by the use of acetone as organic solvent and of water with a conductivity below 0.1 µS/cm as aqueous phase, which is also exemplified as being successful by example 8.

As a further solution of the above described problem, the present invention provides compositions comprising (a) a biologically and/or pharmaceutically active drug and (b) a graft copolymer according to the invention and/or a graft copolymer synthesized according to the invention and/or a colloidal drug carrier according to the invention and/or with nanoparticles of a graft copolymer according to the invention and/or with nanoparticles synthesized according to the invention.

As can be understood from the above explanations the graft copolymer according to the invention has been developed to provide a polymer with certain features. These features can be used to prepare compositions with certain characteristics which are due to the presence of such a polymer. The same features characterize colloidal drug carriers and nanoparticles according to the invention. Therefore it is possible to introduce all these kinds of material in respective compositions.

The characteristics of such compositions can be understood by the above explanations, as well. Because of the physicochemical properties of the graft copolymer according to the invention they can incorporate drugs (feature a) which are admixed with these possible materials (b). Thus the drugs will be adhered to or incorporated into a network of the respective polymer, kept stored and released under suitable conditions which allow a hydrolysis of the polymer. Preferably both materials interact synergistically: storage and release properties allow an ameliorated activity profile of the captured and then released drug.

This is extremely valuable for biological and/or pharmaceutical applications. Consequently, in a preferred embodiment such a composition according to the invention is a pharmaceutical composition, especially for the treatment or prophylaxis of a pulmonary disease or for the administration of systemically acting drugs by inhalation, specifically for human patients.

All pharmaceutically active substances are comprised by this embodiment, for the treatment or prophylaxis of basically all kinds of diseases, for humans as well as for animals. However, as explained above the materials according to the invention are preferably free from surfactants which also applies for such pharmaceutical compositions. Therefore they are very useful for the treatment of pulmonary diseases or in general for administration by inhalation.

In a preferred embodiment such a composition is designed to be administered parenterally, mucosally or by inhalation, preferably by inhalation.

Other ingredients of such compositions are in principal known for a person skilled in the art. Certain apparatus have been developed especially for the administration by inhalation, for example dry powder inhalers or nebulizers. An example for such an inhaler is disclosed in Dalby, R., et al. (2004), *Int. J. Pharm.*, vol. 283, pages 1-9.

In a preferred embodiment such a composition is characterized by the fact that the drug is selected from proteins, peptides, especially peptidic hormones, and/or small molecular weight organic molecules, especially with more positively charged groups than negatively charged groups on the surface of the drug molecule.

This means that the polymeric excipient according to the invention can in principal be used as a general drug release system. However, it is preferred to exploit its negative surface charge to interact and thus additionally bind electrostatically drugs which are positively charged.

In a preferred embodiment such a composition is characterized by the fact that the admixed and/or entrapped peptidic hormone is selected from interleukins (IL-1 to IL-15), interferons (IFN), neurotrophins (NT-1 to NT-3), colony-stimulating factors (CSF), epidermal growth factors (EGF), neuronal growth factors, prolactin, luteinizing-hormone-releasing hormone (LH-RH), insulin, somatostatin, glucagon, gastrin, pentagastrin, urogastrone, calcitonin, seretin, enkephalins, endorphins, antiotensins, renin, bradykinin, tyrocidin, gramicidins, erythropoetin (EPO), angiopeptin, hirudin, oxytocin, vasopressin, calcitonin-gene-related peptide (CGRP), brain-derived growth factors (BDGF), their synthetic analogs and modifications, and/or their pharmacologically active fragments.

In an alternative embodiment such a composition is characterized by the fact that the admixed and/or entrapped small molecular weight organic molecule is selected from Salbutamol, Salmeterol, Fenoterol, Indacaterol, Formoterol, Carmoterol, Aclidinium, Ipratropiumbromid, or Tiotropiumbromid, optionally in the form of an acid added salt, because these are very efficient substances to cure certain pulmonary diseases.

Further solutions of the above described problem are provided by the following uses which can be understood on the basis of the above description:

Use of a graft copolymer according to the invention for the preparation of a colloidal drug carrier;

use of a graft copolymer according to the invention for the preparation of nanoparticles and/or self-aggregating colloidal compositions further comprising an active ingredient;

use of a graft copolymer according to the invention and/or a graft copolymer synthesized according to the invention and/or a colloidal drug carrier according to the invention and/or with nanoparticles of a graft copolymer according to the invention and/or of nanoparticles synthesized according to the invention for the preparation of a composition comprising a biologically and/or pharmaceutically active drug for the controlled, especially sustained release of said drug.

The following examples are intended to further explain the underlying invention without any limitation with respect to the scope of protection.

EXAMPLES

Example 1

Synthesis of a Graft Copolymer of Poly(vinyl sulfonic-co-vinyl alcohol)-g-poly(lactide-co-glycolide) Containing Sulfonic Substituents with Negatively Charged Electrolyte Properties (P(VS-VA)-g-PLGA)

Step (a)
Synthesis of a Polyelectrolyte Backbone by Radical Polymerization of Vinyl Acetate and Vinylsulfonic The copolymerization between vinyl acetate and vinylsulfonic acid sodium salt was carried out in an aqueous/methanol medium using APS (5% mol) as initiator. The vinyl acetate was added as methanol solution (0.2 g/ml) and the vinylsulfonic acid was added as 30% aqueous solution. For example, for a molar feed ratio of 4:6 (VS:VAc), 34.27 g VS as 30% aqueous solution, 10 g VA in 50 ml methanol, and 2.21 g APS were used. For other feed ratios, the amounts were modified accordingly. The reaction mixture was kept at 60° C. under $N_2$ for 24 h. Then the crude copolymers were heated to eliminate the unreacted vinylacetate (b.p. 72° C.), which would be harmful to the subsequent hydrolysis reaction. The unreacted vinyl sulfonic sodium was eliminated by ultrafiltration, which was performed four times on each sample (initial concentration: 200 mg polymer in 10 ml water), by using an Amicon stirred ultrafiltration cell model 8010 (Amicon Corp., Beverly, Mass., USA) equipped with a YM1 filter membrane (Amicon, cut off=1,000 g/mol). Finally the crude copolymer solutions can be condensed, e.g. by rotary evaporation.

Step (b)

Partial Hydrolysis of Poly(vinylsulfonic-co-vinylacetate), Leading to Sulfonic Modified Poly(vinyl alcohol) (P(VS-VA))

The crude copolymers (e.g. 2 g) as produced by step (a) were dissolved in water with stirring; the required amount of potassium hydroxide saturated solution in methanol (e.g. 2 ml) was added dropwise. Then the mixture was refluxed overnight at 60° C., which is slightly below the b.p. of methanol (64° C.). The crude copolymers were then precipitated from water to methanol, washed with methanol for several times until alkali was no more detectable. Finally the yellow powders were dried under vacuum to constant weight.

Step (c)

Grafting of Poly(lactide-co-glycolide) (PLGA) to the Sulfonic Modified Poly(vinyl alcohol) Through Ring-Opening Melt Polymerization Under nitrogen the product of step (b) (P(VS-VA), e.g. 1 g P(VS-VA)-2) was charged into a rigorously dried nitrogen flask which was then degassed at 80° C. in a vacuum line for at least 2 h to eliminate trace water in the backbone. Then the required amount of freshly recrystallized monomer (the LA/GA cyclic lactone, e.g. 5.6 g LA and 4.4 g GA) and the solution of the catalyst $SnOct_2$ (e.g. 0.5 mg) in toluene were added. After well mixing, the flask was degassed at 60° C. (because the melting point of GA is 80° C.) in a vacuum line for at least 2 h to eliminate the toluene, and through additional azeotropic action also trace water. Then the flask was immersed into a preheated oil bath (T=130° C.) for mixing the melt monomers and backbone well, finally increasing the temperature to 190° C. and the reaction was allowed to proceed overnight under stirring.

After cooling to room temperature, using a water bath, the resulting products were dissolved in acetone and precipitated in a large amount of water and finally dried under vacuum to constant weight.

This complete 3 step process is described by FIG. 1, without limiting the scope of the claims.

Example 2

Variation of the Feed Monomer Ratio

Example 1 has been carried out with four different feed monomer ratios (a), (b), (c) and (d) of vinyl sulfonic vs. vinyl acetate as outlined in table 1. The determined properties of the polymers according to the invention resulting from this variation are also included in table 1. The determined properties are:

$S^a$: sulphur element analysis after hydrolysis;
$S^b$: theory sulphur content calculated from the feeding on the assumption that the degree of hydrolysis is 100%;
C: copolymer composition, calculated from $^1$H NMR result (compare example 3);
V: intrinsic viscosity, determined with an Ubbelohde viscosimeter (Company Ubbelohde, Germany) from aqueous 0.5N $NaNO_3$ solutions at 25° C. with five different concentrations, given in dl/g.

TABLE 1

The properties of sulfonic modified backbone P(VS-VA)-g-PLGA

| | Feed monomer ratio (VS:VAc) | $S^a$ (%) | $S^b$ (%) | C (VS %) | V (dl/g) |
|---|---|---|---|---|---|
| (a) | 2:8 | 9.9 | 10.4 | 37.8 | 0.162 |
| (b) | 4:6 | 15.4 | 16.3 | 51.8 | 0.065 |
| (c) | 6:4 | 17.2 | 20.1 | 71.8 | 0.053 |
| (d) | 8:2 | 19.7 | 22.7 | 85.9 | 0.040 |

From the intrinsic intrinsic viscosity data in Table 1 it can be seen that the increasing of VS:VA ratio in the backbone leads to decreasing intrinsic intrinsic viscosity. This is an indicator that the function of sulfonic modification increases the hydrophilicity of the backbone.

Example 3

Figure 2:
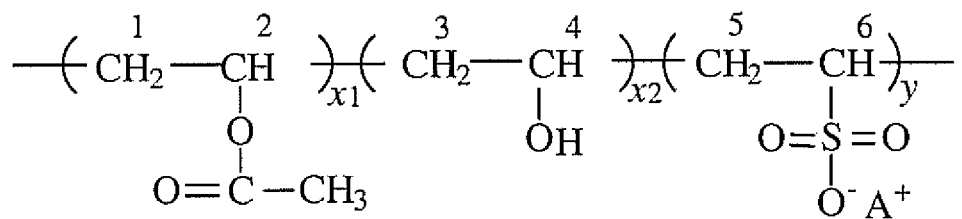
FIG. 2: $^1$H NMR spectra of P(VS-VA) backbone in $D_2O$, of different polymer backbones as prepared by example 3.
  (a) P(VS-VA)-2
  (b) P(VS-VA)-4
  (c) P(VS-VA)-6
  (d) P(VS-VA)-8
Figure 2:
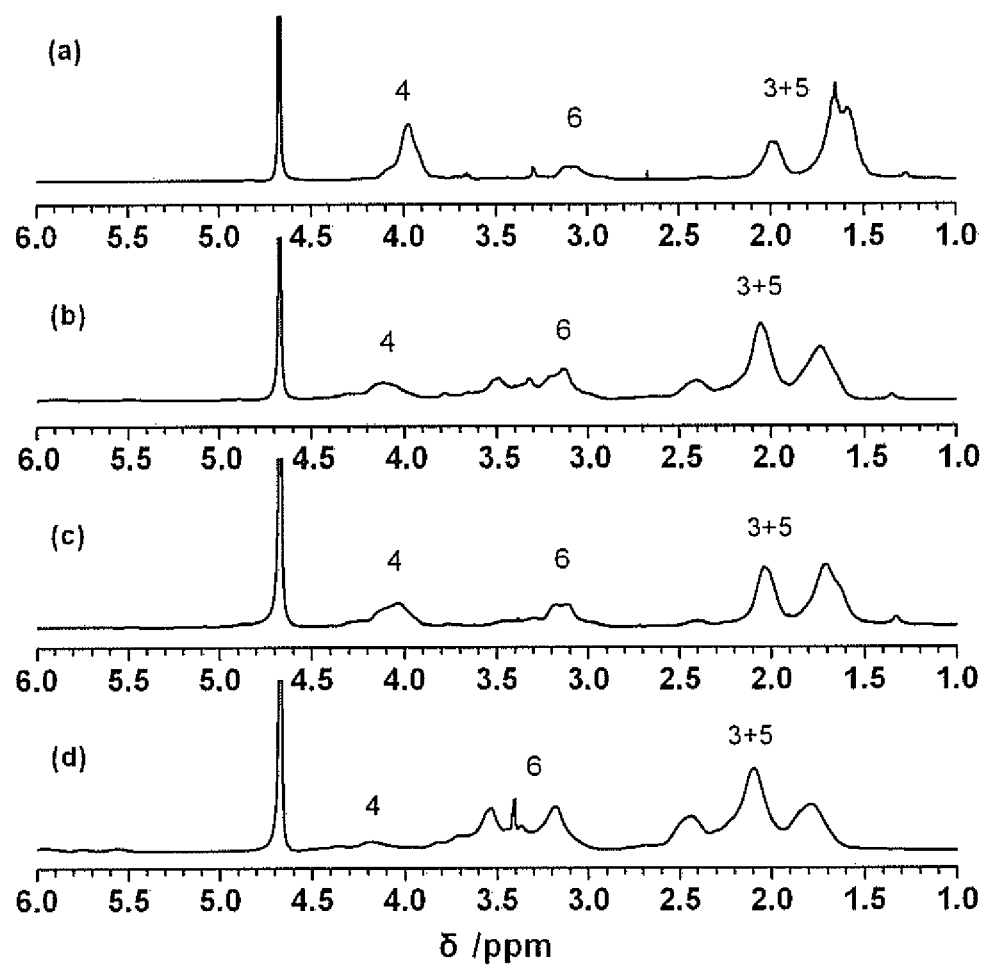

NMR Data for Confirming the Structure of the Backbone and Calculating the Composition of the Backbone FIG. 2 shows the $^1$H NMR spectra of the P(VS-VA) backbones in $D_2O$, prepared according to examples 1 and 2. Protons and the corresponding signals are assigned in the spectra.

It is worth noting that no signals of the PVA backbone connected with acetate groups were visible after hydrolysis (the esterified —CH—$OCOCH_3$ in the range of 4.9 ppm), indicating that the degree of hydrolysis was nearly 100%.

For the methylene (—$CH_2$—) protons, it was not possible to integrate the signals because of their overlapping. Hence, it was not possible to determine the copolymer composition through the integrals of the methylene protons.

For methine (—CH—) protons, the signal of VS group well divided from the VA group, so the copolymer composition of VS was calculated by comparing integrals of characteristic peaks of the CH—OH and the CH—$OCOCH_3$ group near δ=3.8-4.4 ppm and the CH—$SO_3Na$ group δ=2.8-3.6 ppm.

Example 4

FT-Infrared Spectra for Intermediates of the Synthesis Process

Figure 3:
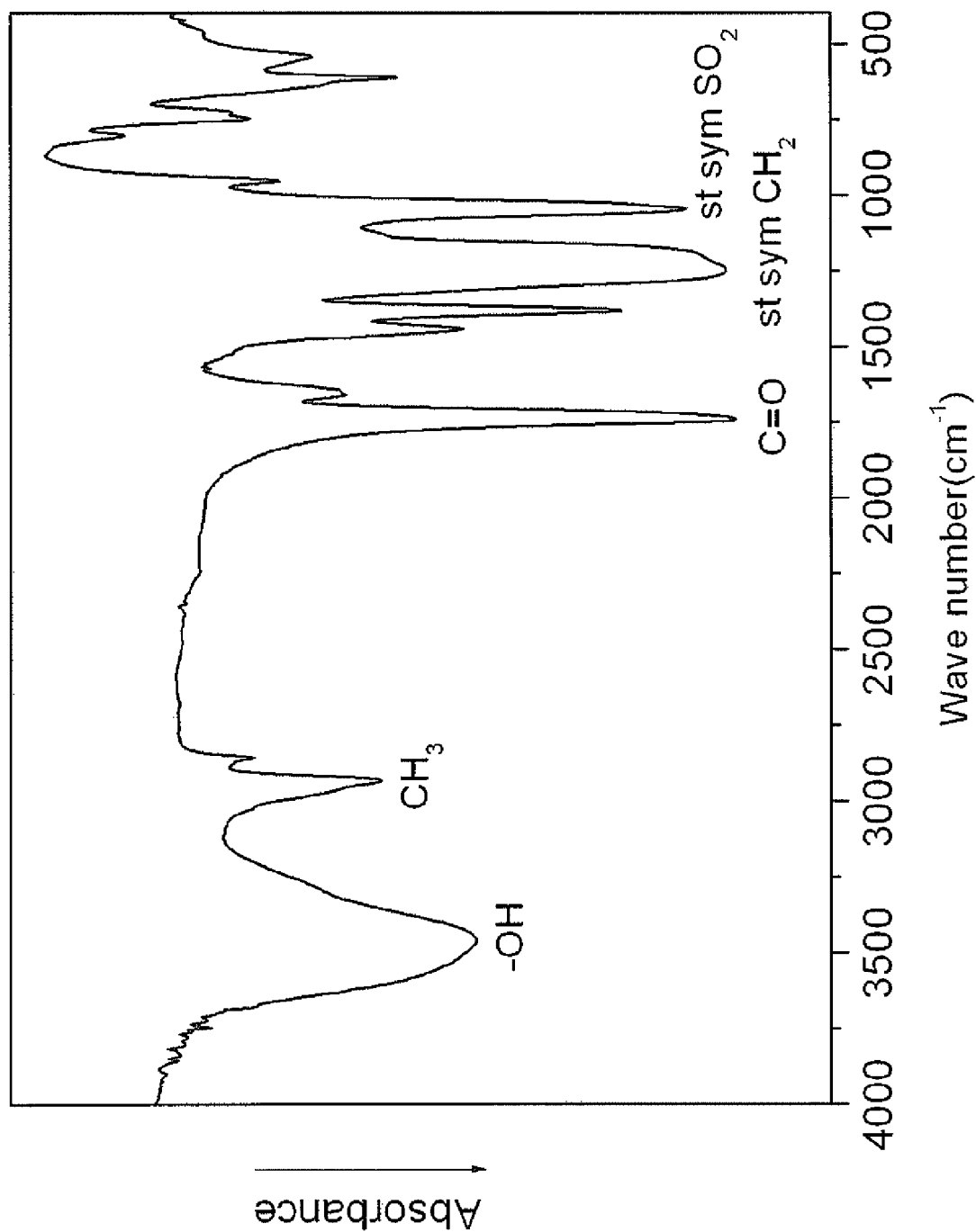
FIG. 3: FT-IR spectrum of P(VS-VAc) (VS:VAc=8:2), before hydrolysis (see example 4).
Figure 4:
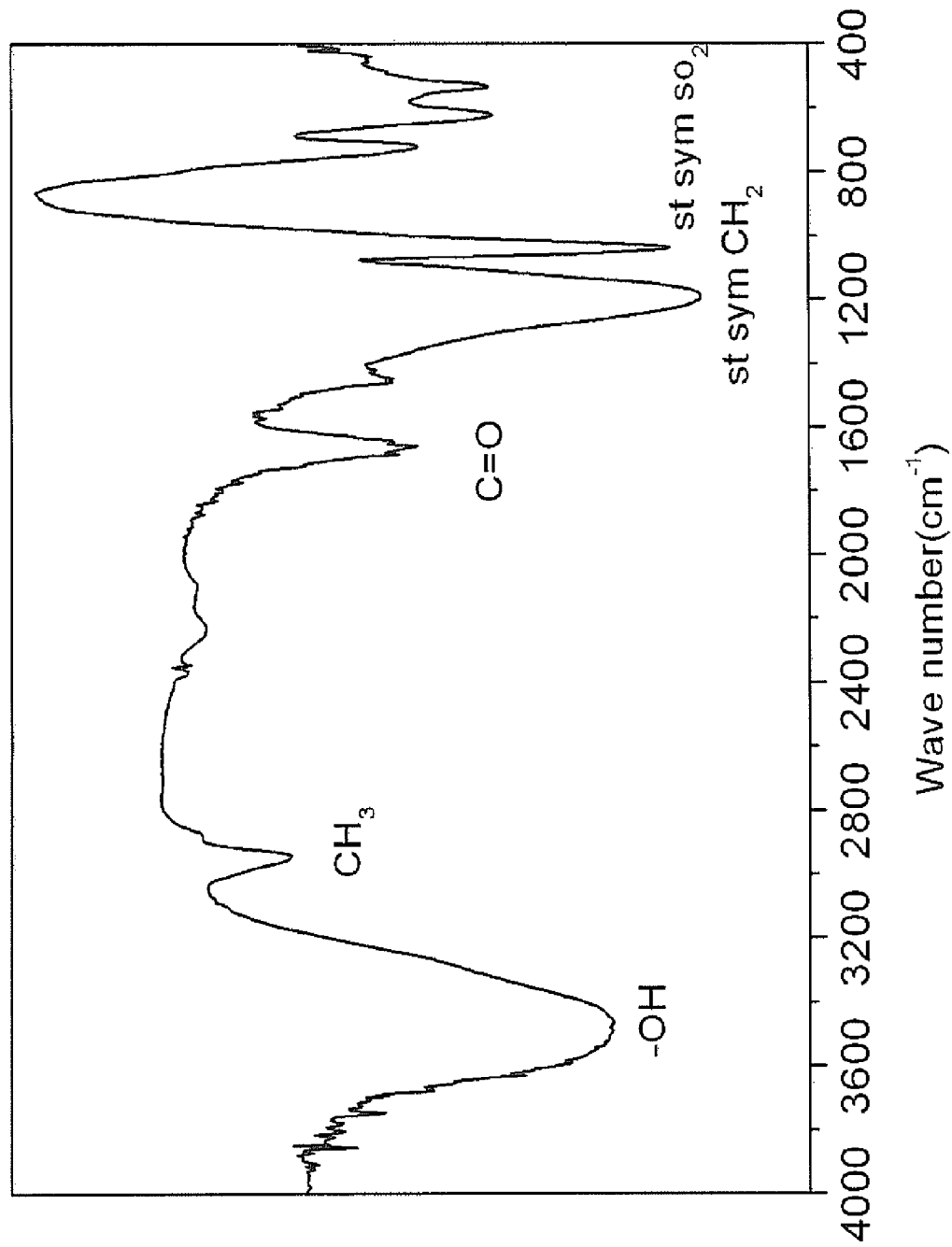
FIG. 4: FT-IR spectrum of P(VS-VAc) (VS:VAc=8:2), after hydrolysis (see example 4).
Figure 5:
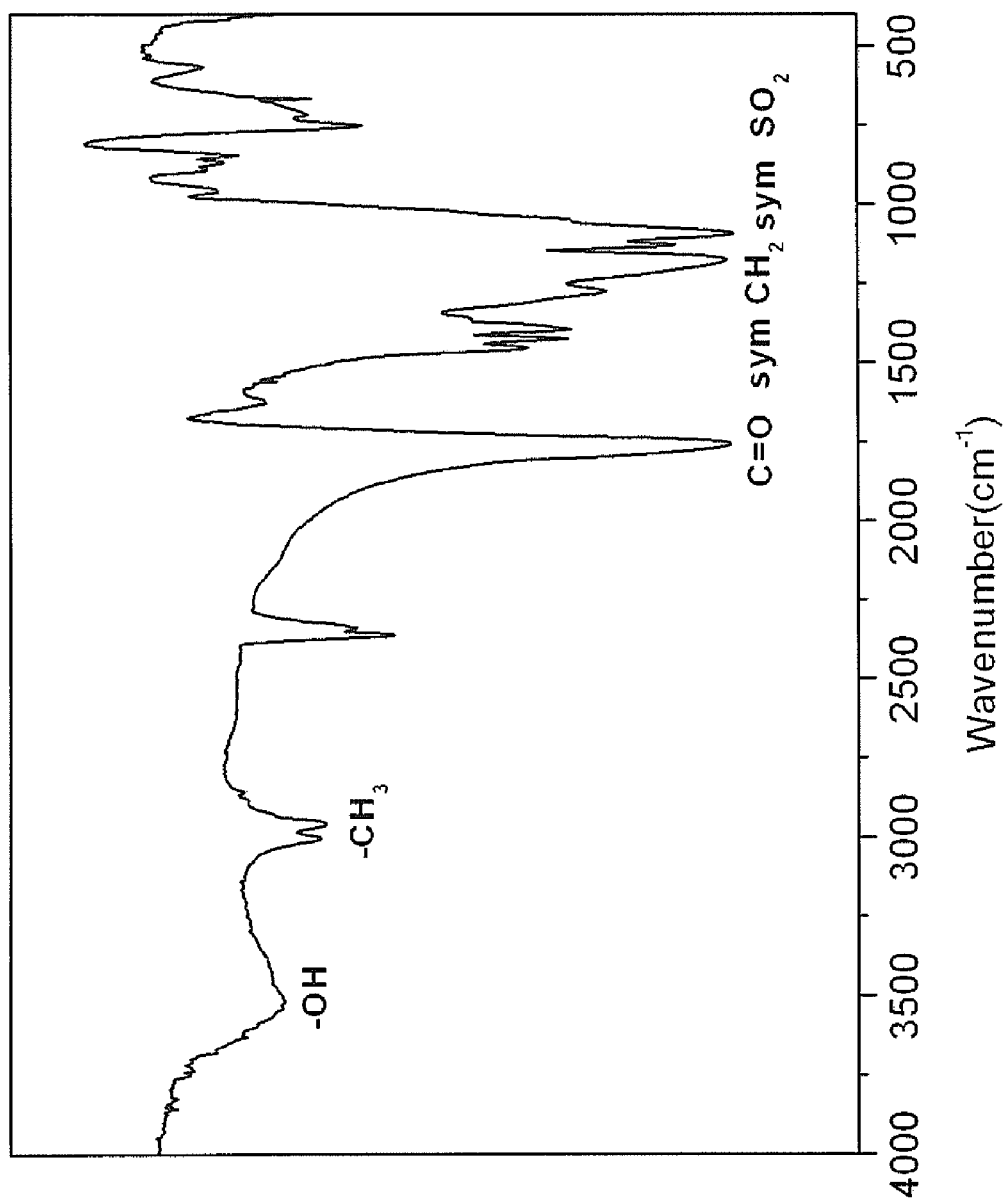
FIG. 5: FT-IR spectrum of P(VS-VA)-g-PLGA(8-10) (see example 4).

During a synthesis of a P(VS-VAc) (VS:VAc=8:2), according to examples 1 and 2, samples have been taken and analyzed by FT-Infrared (KBr) spectroscopy. The resulting spectra are collected in FIGS. 3, 4 and 5.

The major signals can be ascribed to specific wavelengths as follows:

~3500 $cm^{-1}$ (—OH);
~3000 $cm^{-1}$ (—$CH_3$);
~1700 $cm^{-1}$ (C=O);
~1200 $cm^{-1}$ (st sym $CH_2$);
~1040 $cm^{-1}$ (st sym $SO_2$).

As a result, it can be stated that the three steps of the reaction could be confirmed by FT-IR spectroscopy. The absorption peak of the backbone —$CH_2$ group and —$SO_3$ group is present in all the three spectra. After hydrolysis, the relative intensity of hydroxyl increased, and when it was grafted with PLGA the intensity of the —OH group absorption decreased accordingly. In addition, the intensity of carbonyl peak became weaker after hydrolysis with respect to loss of acetate units and became stronger after grafting the backbone with PLGA.

Example 5

NMR Data for Confirming the Graft Structure of the Polyester and Calculating their Composition Further polymers according to the invention have been prepared as described in example 1. For these P(VS-VA):PLGA weight ratios of 1:5, 1:10 and 1:15 have been chosen (further details: see example 6).

Figure 6:
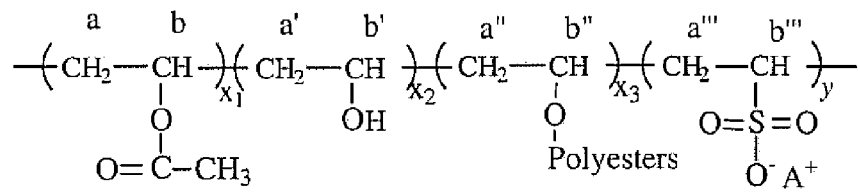
FIG. 6: $^1$H NMR spectrum of P(VS-VA)-g-PLGA(8-10) (see example 5).
Figure 6:
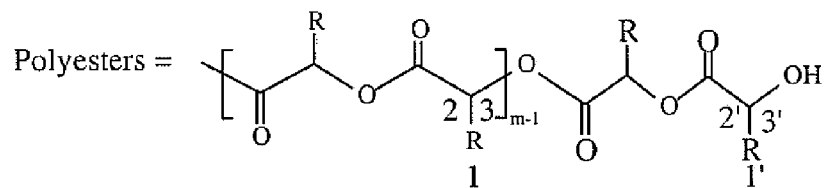
Figure 6:
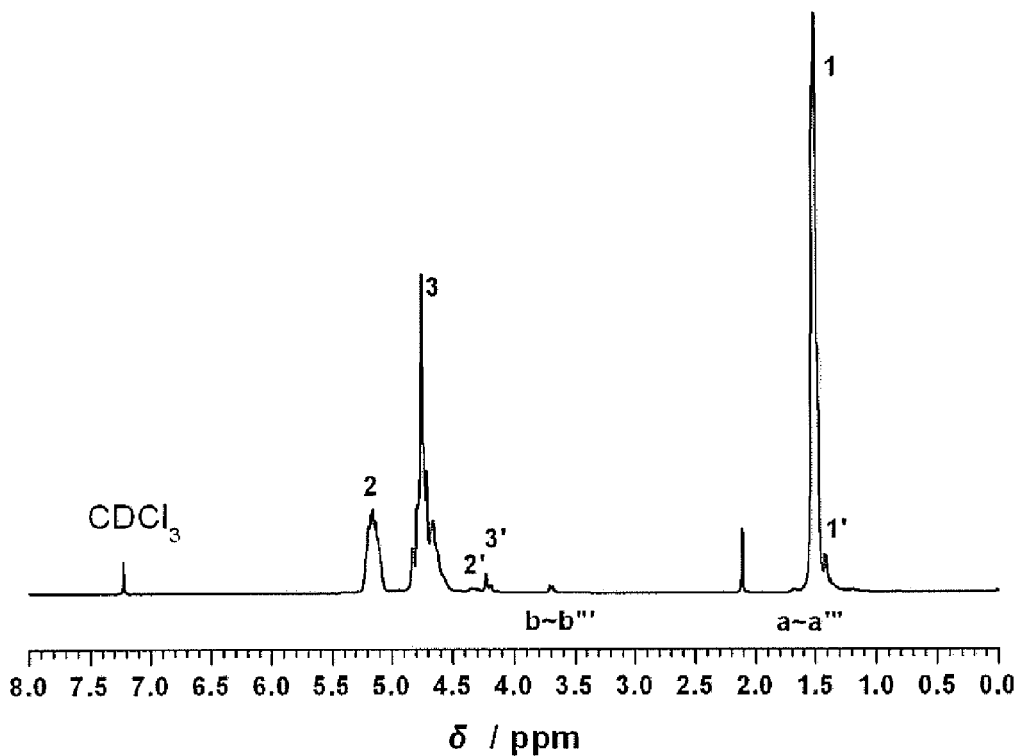
Figure 7:
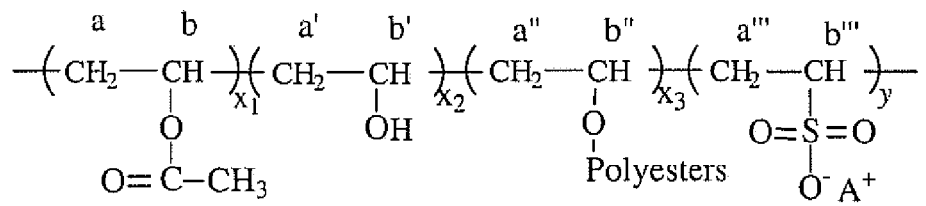
FIG. 7: $^{13}$C NMR spectrum of P(VS-VA)-g-PLGA(8-10) (see example 5).
Figure 7:
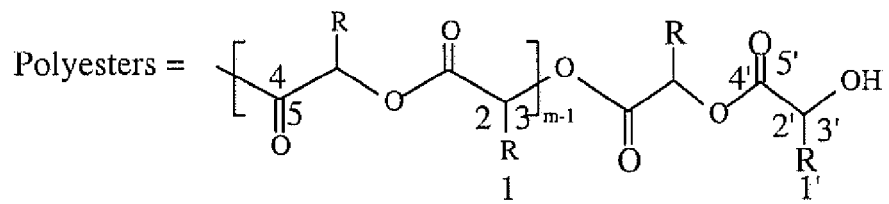
Figure 7:
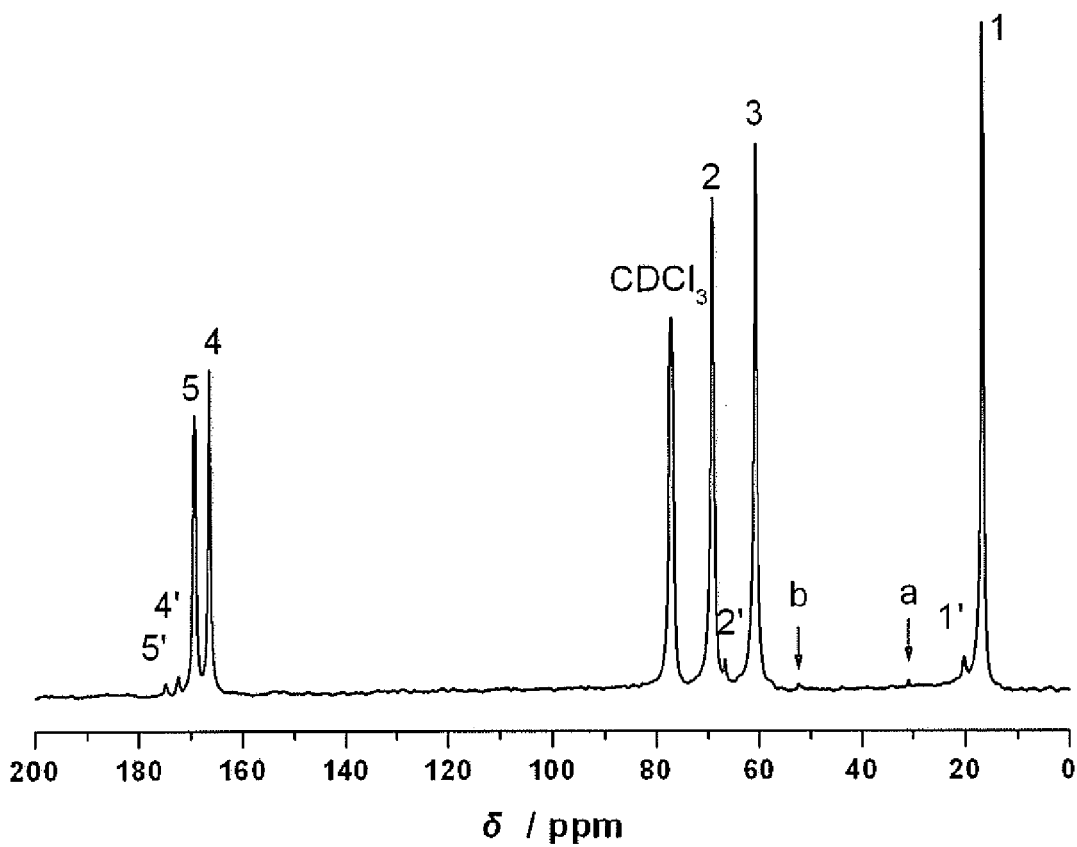

Typical $^1$H NMR analysis and $^{13}$C NMR spectra for one of these reaction products are shown in FIGS. 6 and 7, respectively. The corresponding signals are assigned in the spectra.

In the $^1$H NMR spectrum (FIG. 6), the signal of the hydroxyl terminated lactide units indicate the successful grafting of PLGA to the P(VS-VA) backbone in the polyester. The PLGA units per chain can be obtained by intensity comparison of PLGA chain and its end groups. The LA/GA mol ratio can be obtained by intensity comparison of LA units and GA units.

$$PLGA \text{ side chain length} = \frac{I_{2+3} + I_{2'+3'}}{2I_{2'+3'}}$$

$$\text{Ratio of } LA \text{ vs. } GA: \frac{LA}{GA} = \frac{2I_{1+1'}}{3I_{2+2''}}$$

In the $^{13}$C NMR spectrum (FIG. 7), the signals of PLGA located at 4', 5', 1' result from the end group of the side chain. The signal located at 30 ppm (a) comes from the $CH_2$ group of the backbone, and the signal located at 55 ppm comes from —$CHSO_3Na$ group of the backbone.

Example 6

Physicochemical Properties of the Polyesters with Different Backbone Monomer Ratios and Variation of the Graft PLGA Side Chain Length Further polymers according to the invention have been prepared as described in examples 1, 2 and 5. In this case the weight mol ratios of VAc vs. VS have been chosen as 8:2, 6:4, 4:6 and 2:8, and ratios of P(VS-VA):PLGA have been chosen as 1:5, 1:10 and 1:15 (also discussed in example 5).

The diverse ratios as well as the determined properties of the prepared polymers according to the invention resulting from this variation are summarized in table 2.

The determined properties are:
VAc:VS: mol ratio of backbone monomer in feed;
P(VS-VA):PLGA: weight ratio of backbone vs. PLGA monomers in feed;
PLGA: units per chain, from $^1$H NMR analysis by intensity comparison of PLGA chain and end groups, as described in example 5 and FIG. 6;
LA:GA$^b$: mol ratio of monomer units in the side chain from $^1$H NMR analysis, as described in example 5 and FIG. 6;
$T_g$: Single glass transition temperature ($T_g$) in ° C., as determined from DSC analysis (differential scanning calorimetry)

TABLE 2

Physicochemical properties of the P(VS-VA)-g-PLGA systems

| No. | VAc:VS in feed (mol ratio) | P(VS-VA):PLGA in feed (weight ratio) | PLGA (Units per Chain) | LA:GA (mol %) | $T_g$ (° C.) |
|---|---|---|---|---|---|
| 1 | 8:2 | 1:5 | 15.4 | 54.0:46.0 | 25.9 |
| 2 | 8:2 | 1:10 | 17.4 | 51.9:48.1 | 35.1 |
| 3 | 8:2 | 1:15 | 32.3 | 51.3:48.7 | 37.3 |
| 4 | 6:4 | 1:5 | 9.9 | 50.1:49.9 | 25.5 |
| 5 | 6:4 | 1:10 | 21.1 | 50.4:49.6 | 35.0 |
| 6 | 6:4 | 1:15 | 20.4 | 51.3:48.7 | 35.5 |
| 7 | 4:6 | 1:5 | 14.1 | 50.5:49.5 | 24.9 |
| 8 | 4:6 | 1:10 | 30.1 | 51.6:48.4 | 32.7 |
| 9 | 4:6 | 1:15 | 51.2 | 51.3:48.7 | 38.2 |
| 10 | 2:8 | 1:5 | 21.1 | 50.7:49.3 | / |
| 11 | 2:8 | 1:10 | 41.5 | 54.4:45.6 | 34.4 |
| 12 | 2:8 | 1:15 | 54.4 | 51.4:48.6 | 38.3 |

As evidenced by these data, the variations of the synthesis method according to the invention indeed allow the production of graft polymers with diverse physicochemical properties.

Example 7

Analysis of the Degradation Behavior of P(VS-VA)-PLGA Graft Polymers

In order to analyse the degradation behavior (polymer erosion) of P(VS-VA)-PLGA graft polymers according to the invention, polymer films of these 3 different polymers differing in their degree of sulfonic substitution were selected: P(VS-VA)-PLGA(2-10), P(VS-VA)-PLGA(4-10) and P(VS-VA)-PLGA(6-10). They were produced according to the preceding examples and prepared by casting them from a 5% (w/v) solution in dichloromethane using Teflon™ moulds. After 72 h of drying at a temperature of 4° C. the samples were recovered and discs with a diameter of 17 mm were punched from the polymer films in a semi-dry state using a cork bore. Residual solvents were then removed in vacuo at room temperature until constant weights were obtained.

To determine the in vitro-degradation profiles, weighed film samples (ca. 30 mg each; 3 samples in parallel were placed in 10 ml of phosphate buffered saline in glass vials (PBS, pH 7.4, 0.15 M) and kept at 37° C. in an incubator. The glass vials were shaken gently once a day. The pH of the degradation buffer was periodically monitored and was found to be >6.8 after the study period of 21 days for all polymers tested. After 2, 7, 14 and 21 days, samples were recovered, blotted dry with Kimwipes™ and wet weight was measured gravimetrically. Wet samples were then frozen at −80° C., freeze-dried in vacuo for ca. 72 h at room temperature until constant masses were obtained. Polymer mass loss was calculated from the following formula: Mass loss (%)=100−(mass (dry)×100/original mass).

Figure 8:
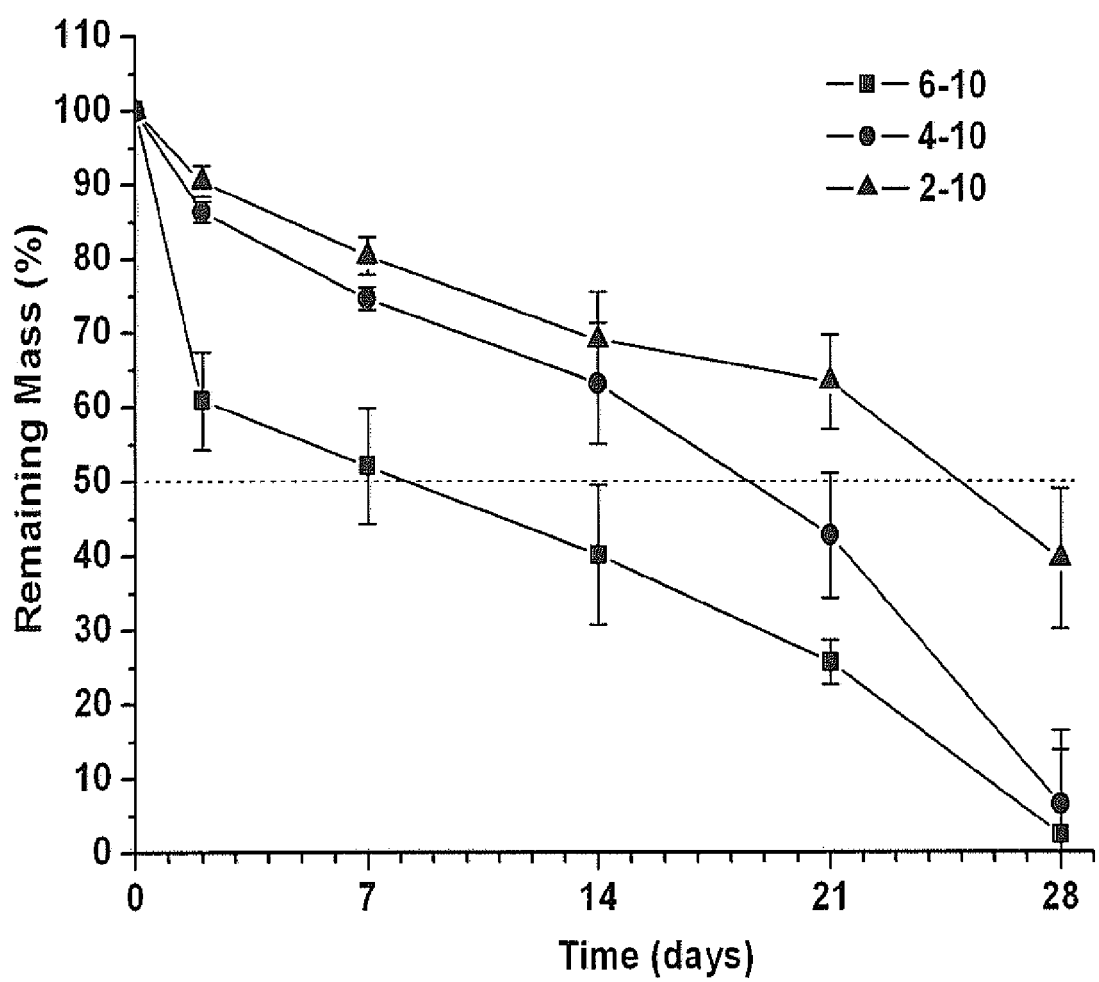
FIG. 8: In vitro-degradation profile of P(VS-VA)-g-PLGA. Mass loss of P(VS-VA)-g-PLGA(2-10), P(VS-VA)-g-PLGA(4-10) and P(VS-VA)-g-PLGA(6-10) as a function of time, during incubation in PBS (pH 7.4; 37° C.; see example 7).

The results are summarized in table 3 and shown graphically in FIG. 8. In this figure the value of 50% remaining mass is shown by a dotted line.

TABLE 3

In vitro-degradation profile of P(VS-VA)-g-PLGA.

| Time (days) | P(VS-VA)-g-PLGA (2-10) | P(VS-VA)-g-PLGA (4-10) | P(VS-VA)-g-PLGA (6-10) |
|---|---|---|---|
| 0 | 100 | 100 | 100 |
| 2 | 91/2.1 | 86/1.4 | 61/6.5 |

TABLE 3-continued

In vitro-degradation profile of P(VS-VA)-g-PLGA.

| Time (days) | P(VS-VA)-g-PLGA (2-10) | P(VS-VA)-g-PLGA (4-10) | P(VS-VA)-g-PLGA (6-10) |
|---|---|---|---|
| 7  | 81/2.5 | 75/1.5 | 52/7.8 |
| 14 | 69/6.4 | 63/8.1 | 40/9.4 |
| 21 | 65/6.3 | 42/8.4 | 35/3.0 |
| 28 | 40/9.5 | 7/10   | 3/11.5 |

Mass loss of graft polymers according to the invention as a function of time, during incubation in PBS (pH 7.4; 37° C.), with the standard deviation given as the second number.

These date demonstrate that the polymer with higher degree of sulfonic substitution, P(VS-VA)-PLGA(6-10), showed the highest erosion with a degradation half-life around 8 days. P(VS-VA)-PLGA(4-10) had a half-life of ca. 18 days, while P(VS-VA)-PLGA(2-10) had a half-life of ca. 25 days.

Factors contributing to degradation properties of those amphiphilic polyesters are by random hydrolytic ester bond cleavage of PLGA side chain by diffusion or matrix swelling. The hydrophilic/hydrophobic balance affected the degradation behavior, increasing the hydrophilicity of the polymeric matrix, the diffusion or matrix swelling rate increased, which led to accelerated degradation time.

Figure 9:
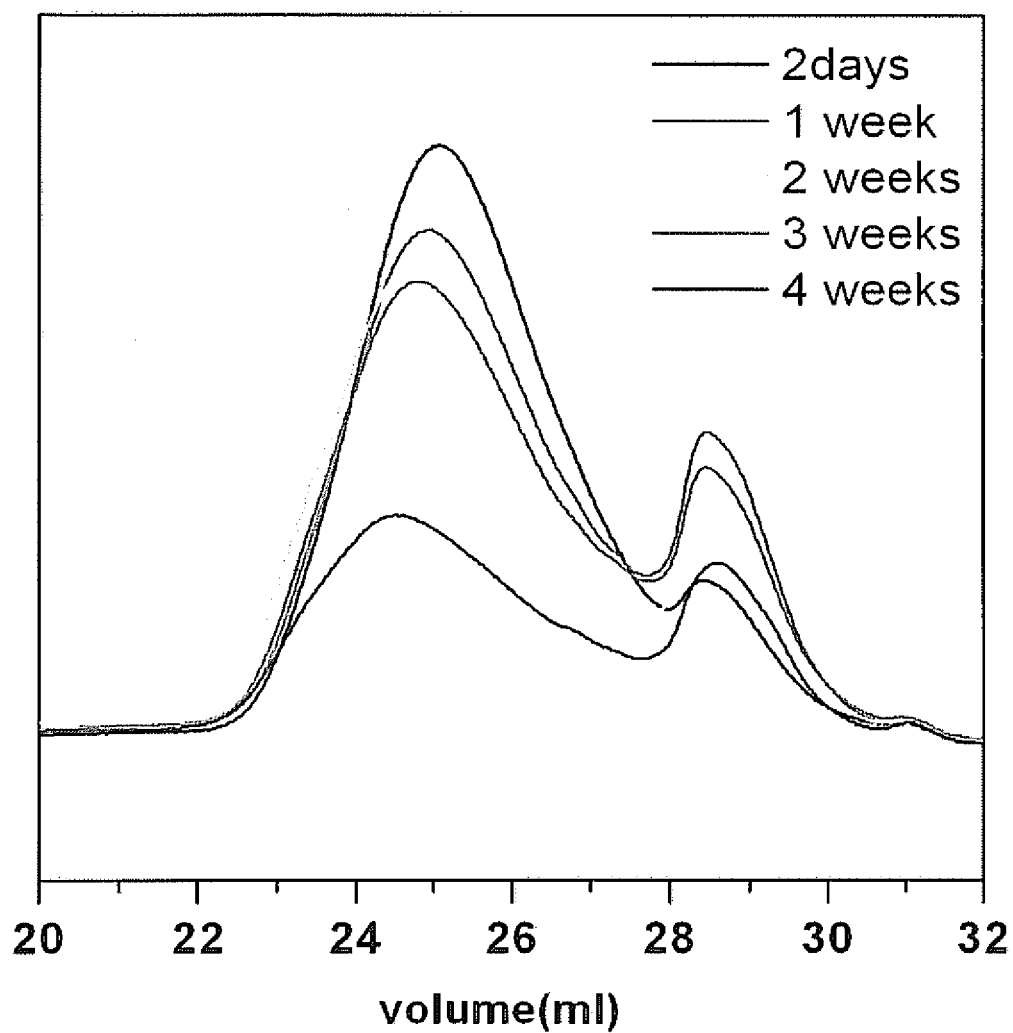
FIG. 9: GPC profiles of P(VS-VA)-PLGA(2-10) during the degradation, measured after 2 days, 1 week, 2 weeks, 3 weeks and 4 weeks (see example 7).

FIG. 9 illustrates the structural changes that take place during the degradation process, exemplified by P (VS-VA)-PLGA(2-10): in the GPC profile the main peak, due to the intact polymer decreases while the peak for low molecular weight compound increases in the course of the monitored 4 weeks.

Example 8

Preparation of P(VS-VA)-G-PLGA-Nanoparticles

Based on the amphiphilicity of the graft polyesters, nanoparticles were prepared by the solvent displacement technique as described in the following. The principle of this reaction as well as methods to analyse the products are described e.g. in this publication: Jung T. et al. (2000); Sulfobutylated poly(vinyl alcohol)-graft-poly(lactide-co-glycolide)s facilitate the preparation of small negatively charged biodegradable nanospheres; *J. Controlled Release*; vol. 67, pages 157-169.

For this purpose, in parallel experiments 10.0 mg of 5 different polymers produced according to the preceding examples were taken. Each 10.0 mg sample was dissolved in 1 ml of acetone at 25° C. The resulting solution was subsequently injected to a magnetic stirred (500 rpm) aqueous phase of 5 ml filtrated and double distilled water (pH 7.0, conductance 0.055 μS/cm, 25° C.) using an electronically adjustable single-suction pump and an injection needle (Sterican 0.55×25 mm), operated at constant flow rate (10.0 ml/min). The pump rate was regulated and constantly monitored by an electric power control. After the injection of the organic phase the resulting colloidal suspension was stirred for 8 h under reduced pressure to remove the organic solvent. Particles were characterized and used directly after preparation. The properties of the nanoparticles were evaluated in terms of mean particle size, size distribution (given as polydispersity index), zeta-potential in distilled water and SEM (scanning electron miscroscope) images.

The physicochemical properties of the resulting particles are summarized in table 4.

TABLE 4

Mean particle size, polydispersity index and ζ-potential of nanoparticles

| No. | Polymer type | Mean particle size (nm) | Polydispersity Index | ζ-potential (mV) |
|---|---|---|---|---|
| 1 | P(VS-VA)-g-PLGA(6-5)  | 151 ± 2.340  | 0.091 ± 0.017 | −25.6 ± 0.421 |
| 2 | P(VS-VA)-g-PLGA(6-10) | 138 ± 1.240  | 0.085 ± 0.015 | −30.6 ± 0.514 |
| 3 | P(VS-VA)-g-PLGA(6-15) | 134 ± 0.455  | 0.080 ± 0.016 | −27.7 ± 0.534 |
| 4 | P(VS-VA)-g-PLGA(2-10) | 120 ± 0.898  | 0.072 ± 0.003 | −19.2 ± 0.168 |
| 5 | P(VS-VA)-g-PLGA(4-10) | 139 ± 0.478  | 0.087 ± 0.013 | −25.9 ± 0.816 |

Figure 10:
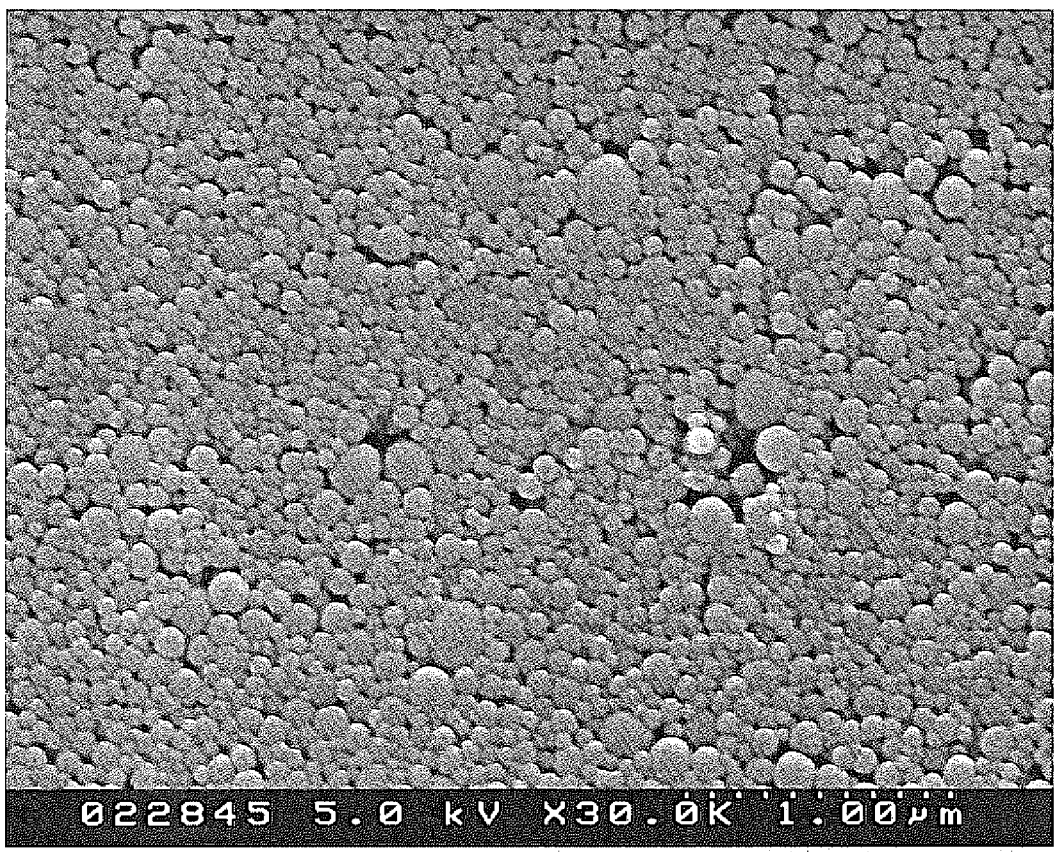
FIG. 10: SEM (scanning electron microscope) image of P(VS-VA)-g-PLGA(6-10) nanoparticles (see example 8).

A SEM image of the polymer P(VS-VA)-g-PLGA(6-10) as one typical example with respect to the mean particle size is shown in FIG. 10.

As can be seen from table 3, stable nanoparticle suspensions with narrow size distribution were obtained at high reproducibility. Increased degree of sulfonic substitution of P(VS-VA)-g-PLGA (compare nos. 1, 2 and 3) decreased the zeta-potential. However, only small differences in mean particle size were observed. The size data shown in table 3 are in agreement with the SEM observation, which also demonstrates (FIG. 8) regular spherical particle morphology.

The invention claimed is:

1. A graft copolymer of poly(vinyl sulfonic-co-vinyl alcohol)-g-poly(lactide-co-glycolide) (P(VS-VA)-g-PLGA) with negatively charged electrolyte properties.

2. The graft copolymer according to claim 1 described by formula (I):

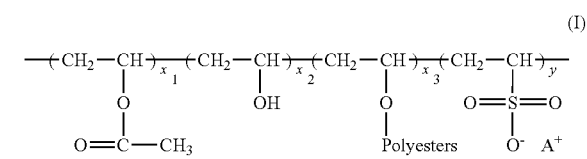

(I)

wherein $A^+$ is selected from $Na^+$, $K^+$, $Li^+$, $NH_4^+$, or any other monovalent cation, the number of monomer units (x1+x2+x3+y) is equal or below 1 000, the mol ratio (x1+x2+x3)/y is from 10/1 to 1/10, the mol ratio x2/x3 is from 0 to 1/10, the mol ratio x1/x3 is from 0 to 1/10, and "Polyesters" is a random homo- or co-polymer described by formula (II):

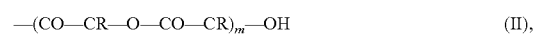

(II), wherein
R is H or $CH_3$, and
m is an integer from 1 to 100.

3. The graft copolymer according to claim 2, wherein $A^+$ is $Na^+$ or $K^+$.

4. The graft copolymer according to claim 2, wherein the number of monomer units (x1+x2+x3+y) is equal to or below 300.

5. The graft copolymer according to claim 2, wherein the mol ratio (x1+x2+x3)/y is from 1/5 to 5/1.

6. The graft copolymer according to claim 2, wherein the mol ratio x2/x3 is from 0 to 1/20.

7. The graft copolymer according to claim 2, wherein the mol ratio x1/x3 is from 0 to 1/20.

8. The graft copolymer according to claim 2, wherein the mol weight ratio of the backbone poly(vinyl sulfonic-co-vinyl alcohol), consisting of all groups x1 and x2 and x3 without "Polyesters" and y according to formula (I), vs. graft PLGA, consisting of all groups "Polyesters" according to formulae (I) and (II), (expressed as P(VS-VA):PLGA) is between 1:2 and 1:30.

9. The graft copolymer according to claim 2, wherein m is an integer from 5 to 60.

10. The graft copolymer according to claim 2, wherein the mol ratio of LA (R=$CH_3$)/GA (R=H) is between 0 to 100/1 and 100/1 to 0.

11. The graft copolymer according to claim 1, wherein a glass transition temperature ($T_g$) of the graft copolymer is between 10 and 50° C.

12. The graft copolymer according to claim 1, wherein an intrinsic viscosity of the graft copolymer is between 0.01 and 1.0.

13. The graft copolymer according to claim 1, wherein a 50% degradation time of the graft copolymer is between 2 and 28 days measured under the following conditions:
   a) capture of a polymer film from a 5% (w/v) solution of the graft copolymer according to claim 1 in dichloromethane, resulting in a set of equal samples to be treated in the following steps;
   b) drying for 72 h at a temperature of 4° C.;
   c) removal of residual solvents in vacuo at 25° C. until constant weight;
   d) incubation in 0.15 M phosphate buffered saline (PBS), pH 7.4, at 37° C. and gentle shaking once a day;
   e) recovering of samples at several points in time during the monitored time course;
   f) freeze drying of the recovered samples for ca. 72 h in vacuo at 25° C. until the reach of a constant mass;
   g) and the following calculation:

Mass loss (%)=100−(mass(dry)×100/original mass),
   with:
   mass(dry)=weight after step (f) and
   original mass=weight after step (c).

14. The graft copolymer according to claim 1 wherein the graft copolymer comprises nanoparticles and a mean particle size of the nanoparticles is between 50 and 500 nm.

15. A method for the synthesis of a graft copolymer of poly(vinyl sulfonic-co-vinyl alcohol)-g-poly(lactide-co-glycolide) (P(VS-VA)-g-PLGA) with negatively charged electrolyte properties, comprising:
   a) synthesis of a polyelectrolyte backbone by radical copolymerization of vinyl acetate and a vinylsulfonic acid salt in the presence of a polar solvent and a catalyst, optionally followed by at least one operation selected from the group consisting of isolation, purification, and drying of the synthesis product,
   b) complete or partial hydrolysis or alcoholysis of the poly(vinylsulfonic-co-vinylacetate) synthesis product of (a) under alkaline conditions in the presence of a solvent, optionally followed by at least one selected from the group consisting of isolation, purification and drying of the hydrolysis or alcoholysis product and,
   c) grafting of poly(lactide-co-glycolide) (PLGA) to the sulfonic modified poly(vinyl alcohol) product of b) through ring-opening polymerization in the presence of a catalyst, optionally followed by at least one selected from the group consisting of isolation, purification and drying of the of the grafted product.

16. The method according to claim 15, wherein the polar solvent is at least one selected from the group consisting of water, methanol, ethanol and isopropanol.

17. The method according to claim 15 wherein the radical polymerization catalyst in (a), is ammonium persulfate (APS).

18. The method according to claim 15, wherein the hydrolysis or alcoholysis in (b) is conducted with KOH/$CH_3CH_2OH/H_2O$ or NaOH/$CH_3CH_2OH/H_2O$.

19. The method according to claim 15 wherein the grafting in (c) is conducted with stannous octoate ($Sn(Oct)_2$) as catalyst.

20. The method according to claim 15 comprising:
   a) radical copolymerization of vinyl sulfonic acid sodium and vinyl acetate, according to the following reaction scheme:

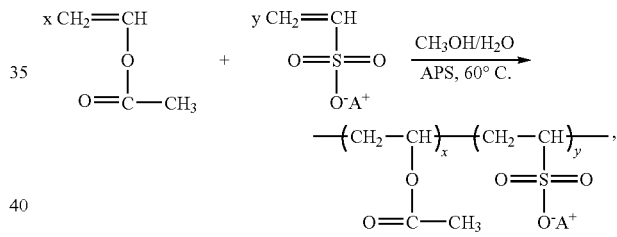

b) hydrolysis to obtain poly(vinyl sulfonic-co-vinyl alcohol), according to the following reaction scheme:

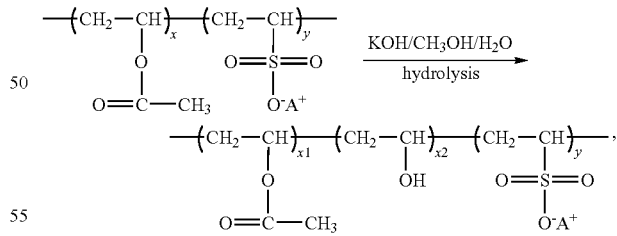

and
   c) grafting with PLGA(LA:GA=50:50), according to the following reaction scheme:

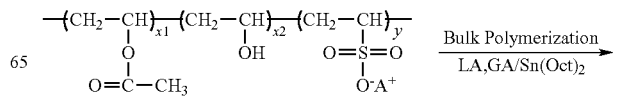

-continued

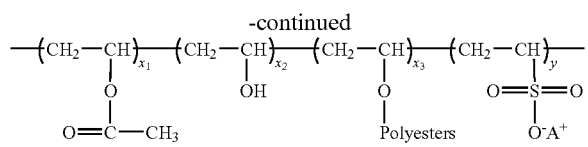

with

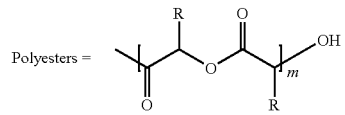

R = H (GA) or CH₃ (LA).

21. The method according to claim 15, wherein a monomer feeding ratio of vinyl sulfonic:vinyl acetate (VSA:VAc) in (a) is between 2:8 and 8:2 in terms of mol %.

22. The method according to claim 15, wherein a graft monomer ratio of lactic acid:glycolic acid (LA:GA) in (c) is between 0 to 100 and 100 to 0.

23. The method according to claim 15, wherein a backbone:graft weight ratio (P(VS-VA):PLGA) in the feed in (c): is between 1:2 and 1:30.

24. A colloidal drug carrier, comprising a graft copolymer according to claim 1.

25. A colloidal drug carrier, comprising a graft copolymer, synthesized according to claim 15.

26. The colloidal drug carrier according to claim 24, which is substantially free from surfactants.

27. Nanoparticles comprising the graft copolymer according to claim 1, wherein a mean particle size of the nanoparticles is between 50 and 500 nm.

28. The nanoparticles according to claim 27 wherein a polydispersity index of the nanoparticles is between 0.05 and 0.1.

29. The nanoparticles according to claim 27 wherein a zeta-potential of the nanoparticles is between −15 and −60 mV.

30. A method for the synthesis of nanoparticles of a graft copolymer with a mean particle site between 50 and 500 nm, comprising:
 a) dissolving the graft copolymer according to claim 1 in an organic solvent,
 b) injecting the solution obtained (a) into an aqueous phase and
 c) removing the organic solvent.

31. The method according to claim 30 wherein the organic solvent is acetone and the aqueous phase is water having a conductivity below 0.1 µS/cm.

32. A composition comprising:
 (a) a biologically and/or pharmaceutically active drug; and
 (b) at least one selected from the group consisting of the graft copolymer according to claim 1, a colloidal drug carrier comprising the graft copolymer according to claim 1 and nanoparticles of the graft copolymer according to claim 1.

33. The composition according to claim 32, which is a pharmaceutical composition, for the treatment or prophylaxis of a pulmonary disease or for the administration of systemically acting drugs by inhalation, for human patients.

34. The composition according to claim 32, wherein the drug is selected from the group consisting of proteins, peptides, peptidic hormones, and small molecular weight organic molecules.

35. The composition according to claim 34, wherein the drug is a peptidic hormone and the peptidic hormone is at least one selected from the group consisting of interleukins (IL-1 to IL-15), interferons (IFN), neurotrophins (NT-1 to NT-3), colony-stimulating factors (CSF), epidermal growth factors (EGF), neuronal growth factors, prolactin, luteinizing-hormone-releasing hormone (LH-RH), insulin, somatostatin, glucagon, gastrin, pentagastrin, urogastrone, calcitonin, seretin, enkephalins, endorphins, antiotensins, renin, bradykinin, tyrocidin, gramicidins, erythropoetin (EPO), angiopeptin, hirudin, oxytocin, vasopressin, calcitonin-gene-related peptide (CGRP), brain-derived growth factors (BDGF), their synthetic analogs and modifications, and their pharmacologically active fragments.

36. The composition according to claim 34, wherein the drug is a small molecular weight organic molecule which is selected from the group consisting of Salbutamol, Salmeterol, Fenoterol, Indacaterol, Formoterol, Carmoterol, Aclidinium, Ipratropiumbromid, and Tiotropiumbromid, wherein the small molecular weight molecule is optionally in the form of an acid added salt.

37. The colloidal drug carrier according to claim 25, which is substantially free from surfactants.

38. Nanoparticles comprising the graft copolymer obtained according to claim 15, wherein a mean particle size of the nanoparticles is between 50 and 500 nm.

39. The nanoparticles according to claim 38 wherein a polydispersity index of the nanoparticles is between 0.05 and 0.1.

40. The nanoparticles according to claim 38 wherein a zeta-potential of the nanoparticles is between −15 and −60 mV.

41. A method for the synthesis of nanoparticles of a graft copolymer with a mean particle site between 50 and 500 nm, comprising:
 a) dissolving the graft copolymer synthesized according to claim 15 in an organic solvent,
 b) injecting the solution obtained in (a) into an aqueous phase and
 c) removing the organic solvent.

42. The method according to claim 41, wherein the organic solvent is acetone and the aqueous phase is water having a conductivity below 0.1 µS/cm.

43. A composition comprising:
 (a) a biologically and/or pharmaceutically active drug and
 (b) at least one selected from the group consisting of the graft copolymer synthesized according to claim 15, a colloidal drug carrier comprising the graft copolymer synthesized according to claim 15 and nanoparticles of the graft copolymer synthesized according to claim 15.

44. The composition according to claim 43, which is a pharmaceutical composition, for the treatment or prophylaxis of a pulmonary disease or for the administration of systemically acting drugs by inhalation, for human patients.

45. The composition according to claim 43, wherein the drug is selected from the group consisting of proteins, peptides, peptidic hormones, and small molecular weight organic molecules.

46. The composition according to claim 45, wherein the drug is a peptidic hormone and the peptidic hormone is at least one selected from the group consisting of interleukins (IL-1 to IL-15), interferons (IFN), neurotrophins (NT-1 to NT-3), colony-stimulating factors (CSF), epidermal growth factors (EGF), neuronal growth factors, prolactin, luteinizing-hormone-releasing hormone (LH-RH), insulin, somatostatin, glucagon, gastrin, pentagastrin, urogastrone, calcitonin, seretin, enkephalins, endorphins, antiotensins, renin, bradykinin, tyrocidin, gramicidins, erythropoetin (EPO), angiopeptin, hirudin, oxytocin, vasopressin, calcitonin-gene-related peptide (CGRP), brain-derived growth factors (BDGF), their synthetic analogs and modifications, and their pharmacologically active fragments.

47. The composition according to claim 45, wherein the drug is a small molecular weight organic molecule which is selected from the group consisting of Salbutamol, Salmeterol, Fenoterol, Indacaterol, Formoterol, Carmoterol, Aclidinium, Ipratropiumbromid, and Tiotropiumbromid, wherein the small molecular weight molecule is optionally in the form of an acid added salt.

48. The composition according to claim 34, wherein the drug comprises molecules having more positively charged surface groups than negatively charged surface groups.

49. The composition according to claim 45, wherein the drug comprises molecules having more positively charged surface groups than negatively charged surface groups.

* * * * *